US012590209B2

(12) United States Patent
Carter et al.

(10) Patent No.: US 12,590,209 B2
(45) Date of Patent: Mar. 31, 2026

(54) PIGMENTED AND FLUORESCENT COMPOUNDS DERIVED FROM THE ADDITION OF A PRIMARY OR SECONDARY AMINE TO AN ALDEHYDE

(71) Applicant: REGENTS OF THE UNIVERSITY OF MINNESOTA, Minneapolis, MN (US)

(72) Inventors: Clay Jeremy Carter, Minneapolis, MN (US); Adrian Hegeman, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 787 days.

(21) Appl. No.: 17/636,729

(22) PCT Filed: Aug. 21, 2020

(86) PCT No.: PCT/US2020/047488
§ 371 (c)(1),
(2) Date: Feb. 18, 2022

(87) PCT Pub. No.: WO2021/035176
PCT Pub. Date: Feb. 25, 2021

(65) Prior Publication Data

US 2022/0289981 A1 Sep. 15, 2022

Related U.S. Application Data

(60) Provisional application No. 62/889,998, filed on Aug. 21, 2019, provisional application No. 62/971,113, filed on Feb. 6, 2020.

(51) Int. Cl.

| | |
|---|---|
| ***C07C 251/16*** | (2006.01) |
| ***C07C 251/30*** | (2006.01) |
| ***C07D 207/20*** | (2006.01) |
| ***C07D 207/22*** | (2006.01) |
| ***C07D 207/44*** | (2006.01) |
| ***C07D 209/08*** | (2006.01) |
| ***C07D 209/20*** | (2006.01) |
| ***C07D 209/42*** | (2006.01) |
| ***C07D 233/64*** | (2006.01) |
| ***C07H 5/04*** | (2006.01) |
| ***C09B 23/06*** | (2006.01) |
| ***G01N 31/22*** | (2006.01) |

(52) U.S. Cl.
CPC ............ *C09B 23/06* (2013.01); *C07C 251/16* (2013.01); *C07C 251/30* (2013.01); *C07D 207/20* (2013.01); *C07D 207/22* (2013.01); *C07D 207/44* (2013.01); *C07D 209/08* (2013.01); *C07D 209/20* (2013.01); *C07D 209/42* (2013.01); *C07D 233/64* (2013.01); *C07H 5/04* (2013.01); *G01N 31/22* (2013.01)

(58) Field of Classification Search
CPC ... C07C 251/16; C07C 251/30; C07D 207/20; C07D 207/22; C07D 207/44; C07D 209/08; C07D 209/20; C07D 209/42; C07D 233/64; C07H 5/04; C09B 23/06
See application file for complete search history.

(56) References Cited

U.S. PATENT DOCUMENTS 3,657,350 A 4/1972 Mooradian et al.
2015/0065531 A1 3/2015 Connor et al.

FOREIGN PATENT DOCUMENTS

EP 0066872 A1 * 8/1981 ............. A01N 35/10

OTHER PUBLICATIONS

PubChem CID 3613299, National Center for Biotechnology Information. PubChem Compound Summary for CID 3613299, 3-(4-Chlorophenyl)prop-2-en-1-imine. https://pubchem.ncbi.nlm.nih.gov/compound/3-_4-Chlorophenyl_prop-2-en-1-imine. Accessed Nov. 4, 2024, create date Sep. 9, 2005. (Year: 2005).*
PubChem CID 136462960, National Center for Biotechnology Information. PubChem Compound Summary for CID 136462960, 4-[(Z)-3-(2-hydroxyethylimino)prop-1-enyl]-2-methoxyphenol. https://pubchem.ncbi.nlm.nih.gov/compound/136462960. Accessed Jan. 22, 2025, create date Jan. 23, 2019. (Year: 2019).*
PubChem CID 127027004, National Center for Biotechnology Information. PubChem Compound Summary for CID 127027004, 2-[[(E)-3-(4-methoxyphenyl)prop-2-enylidene]amino]acetic acid. https://pubchem.ncbi.nlm.nih.gov/compound/127027004. Accessed Jan. 23, 2025, create date Jun. 6, 2017. (Year: 2017).*
Mohyeldin et al., European Journal of Medicinal Chemistry (2016), 118, pp. 299-315. (Year: 2016).*
Childs, R. , et al., "Photochemical and Thermal Stereomutations of 3-Aryl-2-propenylideniminium Salts", J. Am. Chem. Soc. 105, 5041-5046 (1983).
Childs, R., et al., "The Structures of some Iminium Salts. Crystal Structures and C NMR studies of 3-aryl-2-propenylideniminium salts", Journal of Crystallographic and Spectroscopic Research 15(1), 73-87 (1985).

(Continued)

*Primary Examiner* — Laura L Stockton
(74) *Attorney, Agent, or Firm* — Viksnins Harris Padys Malen LLP

(57) ABSTRACT

The invention provides a compound of formula (I): wherein R1, R2, and R3 have any of the values described in the specification, as well as compositions comprising a compound of formula (I), methods for preparing compounds of formula (I), and methods for detecting the presence of an amine in a sample. The compounds are useful as pigments.

18 Claims, 14 Drawing Sheets

Specification includes a Sequence Listing.

(56) References Cited

OTHER PUBLICATIONS

Wang, H. , et al., "Design of cinnamaldehyde amino acid Schiff base compounds based on the quantitative structure-activity relationship", Royal Society Open Science 4(9), 1-11 (2017).

Amirkia, V , et al., "Alkaloids as drug leads—A predictive structural and biodiversity-based analysis", Phytochemistry Letters 10, 6 pages (2014).

Boucherle, B , et al., "Occurrences, biosynthesis and properties of aurones as high-end evolutionary products", Phytochemistry 142, 92-111 (2017).

Ertekin, K , et al., "A Long Wavelength Excitable Fluorophore; Chloro Phenyl Imino Propenyl Aniline (CPIPA) for Selective Sensing of Hg (II)", J Fluoresc 20, 533-540 (2010).

Hansen, D , et al., "Mauritian coloured nectar no longer a mystery: a visual signal for lizard pollinators", Biology Letters 2, 165-168 (2006).

Olesen, J , et al., "Mauritian red nectar remains a mystery", Nature 393, 529 (1998).

Patent Cooperation Treaty , International Search Report and Written Opinion for PCT/US2020/047488, 12 pages dated Feb. 4, 2021.

Pubchem , CID 119216, 12 pages (Create date Mar. 27, 2005; Modify date Oct. 31, 2020).

Pubchem , CID 134923811, 8 pages (Create date Nov. 30, 2019; Modify date Oct. 31, 2020).

Pubchem , CID 136417125, 7 pages (Create date Jan. 23, 2019; Modify date Oct. 31, 2020).

* cited by examiner

Nesocodin-OH

Nesocodin-O⁻

Sinapaldehyde-OH

Sinapaldehyde-O⁻

Sinapaldehyde

Nesocodin
(Sinapaldehyde + L-proline)

1 mM sinapaldehyde in 50 mM Na(H)$CO_3$ pH 9.0, incubated for ~30 min 1 mM sinapaldehyde + 10mM L-proline in 50 mM Na(H)$CO_3$ pH 9.0, incubated for ~30 min 1 mM coniferaldehyde and 10 mM indoline mixed in 200 mM buffers (aqueous) at the respective pHs and then diluted 1:9 in the respective buffer prior to reading.

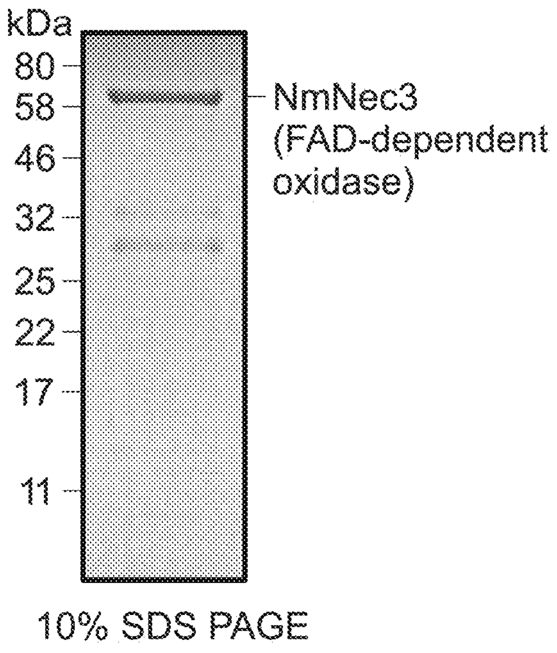

Figure 11A

MATMAILQRTFSFILIFSIALHLKSLFAMETDSGA
ELKYLELIHEANEFTPDEEYDYIVVGGGTAGCPLA
ATLSENYSVLVLERGGDQHSHPNIIRQENVANNAL
PADDENSPSQAFTSEDGVPGLVRGRVLGGSSMINF
GFYSRGDDYFFKNTGIEWDMDSVKTAYEWVEETLV
HRPDNVSTWESSVRDALLEVGVLPDNGNTLDHLVG
TKVSGSTFDSTGNRHGAVELLNKANPNNLRVIVHA
TVDRIIFSSSESSGPSVVRVVYHDSHGKSYQVGIR
ENGEVILSAGAFGSPQLLLVSGVGPSQNLTSLEIP
VVHDQPFVGQYMIDNPRINLALMLPFSVVDSGTPV
VGITGKGSYIETTSSSTPFTSPVSPLYFPYPYPPV
NISMGYFFGKVSNPTSAGSLWLKSPSDVAITPSVR
FNYFSKPEDVHQCADAVATYEKILKTKAMEMYKFK
DHGGEKYFQIVGRQIPENTSDFESMATYCRKTVTT
FYHYCGGCTVNKVVDSNLKVVGIGGLRVVDNSVFT
SSPGTNPQATTMMLGRYMGVKIQQERAGSDGDN

Figure 11B

PIGMENTED AND FLUORESCENT COMPOUNDS DERIVED FROM THE ADDITION OF A PRIMARY OR SECONDARY AMINE TO AN ALDEHYDE

CROSS-REFERENCE TO RELATED APPLICATION

This application is a 35 U.S.C. § 371 application of International Application No. PCT/US2020/047488, that was filed on Aug. 21, 2020, which claims priority to U.S. Provisional Application No. 62/889,998 that was filed on Aug. 21, 2019 and U.S. Provisional Application No. 62/971,113 that was filed on Feb. 6, 2020. The entire content of the applications referenced above is hereby incorporated by reference herein.

STATEMENT REGARDING FEDERALLY SPONSORED RESEARCH

This invention was made with government support under IOS1339246 awarded by the National Science Foundation. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 23, 2020, is named 09531_484WO1_SL.txt and is 5,265 bytes in size.

BACKGROUND OF THE INVENTION

The floral nectar of *Nesocodon mauritianus* has a deep-red color that is attractive to its pollinators. In 1998 it was reported that the nectar pigment was an aurone, however, this was found to be incorrect. Recent studies by the inventors have shown the correct structure of this pigment (termed 'nesocodin') and is an alkaloid/phenylpropanoid mixture of E- and Z-isomers produced by the formation of an imine (or Schiff base) condensation product of sinapaldehyde and proline who's equilibrium shifts to favor the condensed product with increasing pH and/or removal of water from the reaction.

Currently there is a need for the modifications of the natural precursors to synthesize non-natural compounds that still behave similarly to the natural pigment.

SUMMARY OF THE INVENTION

In one aspect the present invention provides compounds that are fluorescent and that are useful as pigments.

Accordingly, the invention provides a compound of formula (I):

(I)

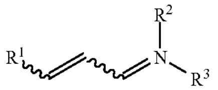

wherein:

$R^1$ is aryl that is substituted with one or more $R^4$, wherein $R^4$ is independently selected from the group consisting of nitro, carboxy, halo, cyano, heteroaryl, aryl, $(C_1\text{-}C_6)$ alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio, $(C_2\text{-}C_6)$alkanoyloxy, —OH, —$NR^aR^b$, —C(═O)NH($C_1$-$C_6$ alkyl)($S(O)_2R^a$), —C(═O)NH($C_1$-$C_6$ alkyl)C(═O)$OR^a$), —C(═O)$NR^aR^b$, —$OS(O)_3R^a$, —C(═O)NH($S(O)_2R^a$), and —C(═O)($C_1$-$C_6$ alkyl), wherein any heteroaryl, aryl, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

$R^2$ is selected from the group consisting of H, residue of an amino acid, residue of saccharide, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

$R^3$ is absent; or $R^3$ is selected from the group consisting of H, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

or $R^2$ and $R^3$ together with the nitrogen to which they are attached form a 4-10 membered ring heterocycle, wherein heterocycle is optionally substituted with one or more groups independently selected from the group consisting of halo, nitro, carboxy, —OH, cyano, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio, $(C_2\text{-}C_6)$alkanoyloxy, —$NR^aR^b$, —C(═O)NH($C_1$-$C_6$ alkyl)$S(O)_2R^a$), —C(═O)NH($C_1$-$C_6$ alkyl)C(═O)$OR^a$), —C(═O)$NR^aR^b$, —$OS(O)_3R^a$, —C(═O)NH($S(O)_2R^a$), and —C(═O)($C_1$-$C_6$ alkyl), wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH, —$NR^aR^b$ and cyano;

provided that when $R^3$ is other than absent, the nitrogen to which $R^3$ is attached is a quaternary nitrogen and is associated with a suitable counter anion $X^-$ to provide a salt;

each $R^a$ and $R^b$ is independently selected from the group consisting of H, $(C_1\text{-}C_6)$alkyl, and $(C_3\text{-}C_6)$cycloalkyl; or $R^a$ and $R^b$ together with the nitrogen to which they are attached form a 4-10 membered ring heterocycle; and X is a suitable counter anion;

provided that the compound is not:

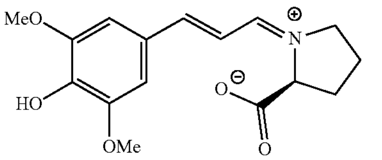

and

Z-isomer

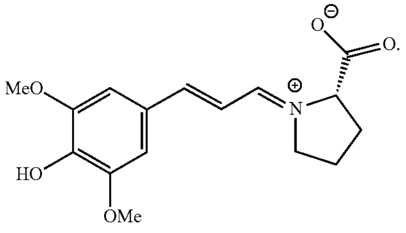

E-isomer

The invention also provides a process for preparing a compound of formula (I) for use as a food dye.

The invention also provides a compound of formula (I), for use as a biodegradable dye.

The invention also provides a compound of formula (I), for use as a detection system for proline and other compounds with primary and secondary amines, and its fluorescent properties.

The invention also provides a compound of formula (I), for use as a red biofilm that may be simultaneously antimicrobial and/or anti-oxidant.

The invention also provides a method for detecting the presence of a primary or secondary amine of formula 3 in a sample:

(3)

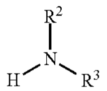

wherein:

$R^2$ is selected from the group consisting of residue of an amino acid, residue of saccharide, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

$R^3$ is selected from the group consisting of H, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

or $R^2$ and $R^3$ together with the nitrogen to which they are attached form a 4-10 membered ring heterocycle, wherein heterocycle is optionally substituted with one or more groups independently selected from the group consisting of halo, nitro, carboxy, —OH, cyano, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio, $(C_2\text{-}C_6)$alkanoyloxy, —$NR^aR^b$, —C(═O)NH($C_1\text{-}C_6$ alkyl)($S(O)_2R^a$), —C(═O)NH($C_1\text{-}C_6$ alkyl)(C(═O)$OR^a$), —C(═O)$NR^aR^b$, —$OS(O)_3R^a$, —C(═O)NH($S(O)_2R^a$), and —C(═O)($C_1\text{-}C_6$ alkyl), wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH, —$NR^aR^b$ and cyano:

comprising:

contacting an aldehyde of formula 2:

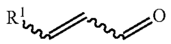

(2)

wherein $R^1$ has any of the values defined above, with the sample under conditions where the aldehyde of formula 2 and the primary or secondary amine of formula 3 form a corresponding compound of formula I; and detecting the presence of the compound of formula I by spectroscopy, wherein the presence of the compound of formula I correlates with the presence of the primary or secondary amine in the sample.

BRIEF DESCRIPTION OF DRAWINGS

FIG. 11A-11B shows the identification of a FAD-dependent oxidase in the raw nectar of *Nesocodon mauritianus*. (A) Protein profile in 9 mL of raw nectar of *Nesocodon mauritianus*. The band corresponding to NmNec3 (largest protein) was excised from the gel and subjected to identification via MS-based proteomics methods. (B) Sequence of NmNec3 (SEQ ID NO:1), which can be purified from the raw nectar of *Nesocodon mauritianus*. The underlined region corresponds to a predicted signal peptide that is cleaved off of the final protein.

DETAILED DESCRIPTION OF THE INVENTION

Figures 1A, 1B:
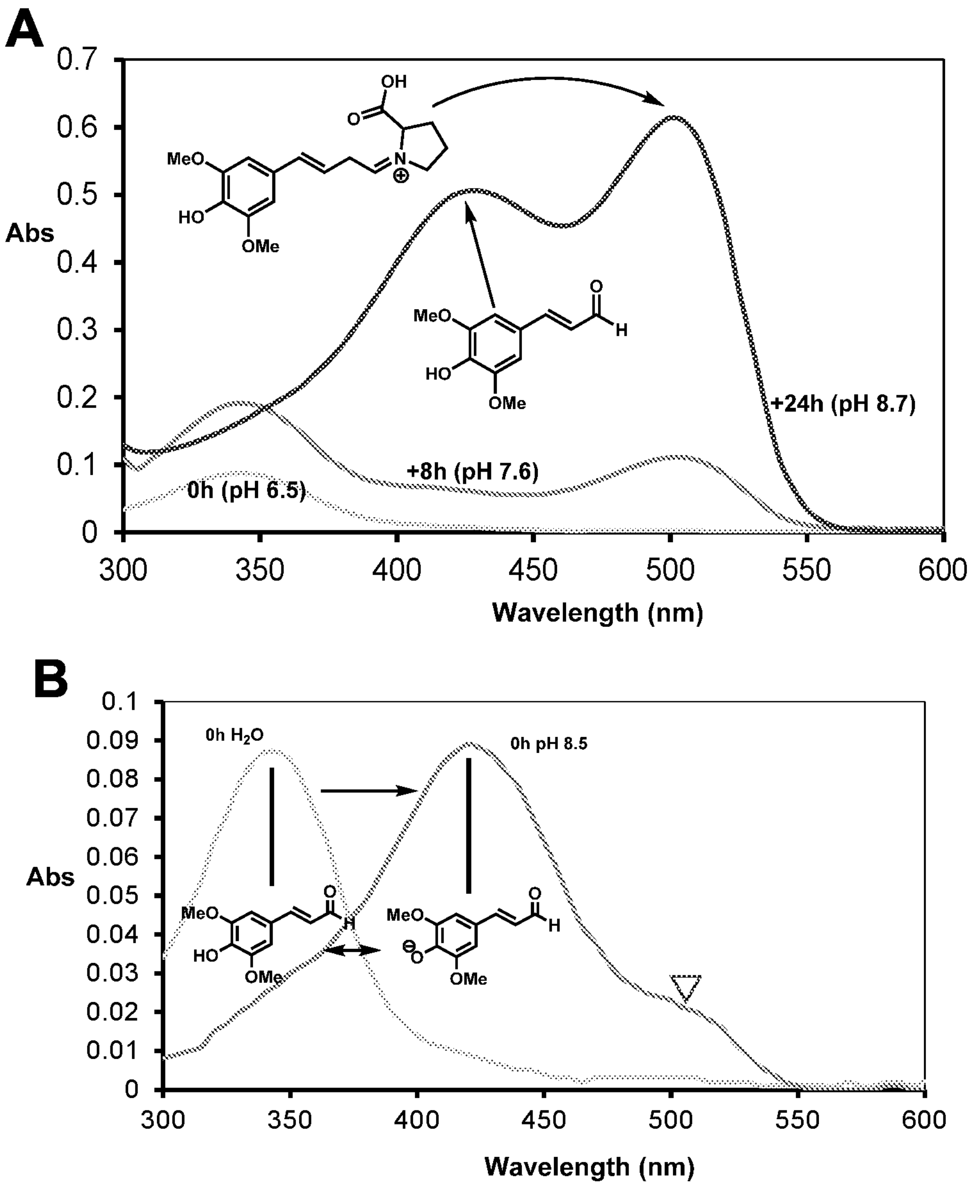
FIGS. 1A-1C show absorbance spectra and pH of nectar collected at 0, +8 hours and +24 hours. (A) Absorbance spectra of nectars collected at 0 hour (yellow), +8 h (orange) and +24 hours (red) after dilution at 1:50 in $diH_2O$. Images of each non-diluted nectar and pH are noted in the inset. (B) Absorbance spectra of 0 h nectar after either being diluted in $diH_2O$ or 50 mM Tricine, pH 8.5. The red arrowhead indicates the location (505 nm) of the predominant peak present in +24 hours nectar. (C) Absorbance spectra of +8 h nectar after either being diluted in $diH_2O$ or 50 mM Tricine, pH 8.5.

The following definitions are used, unless otherwise described: halo or halogen is fluoro, chloro, bromo, or iodo.

Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_5$)alkyl, ($C_2$-$C_5$)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_5$) carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g. tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc.), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc.). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, “heteroaryl” includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. “Heteroaryl” also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term “alkoxycarbonyl” as used herein refers to a group (alkyl)-O—C(═O)—, wherein the term alkyl has the meaning defined herein.

The term “alkanoyloxy” as used herein refers to a group (alkyl)-C(═O)—O—, wherein the term alkyl has the meaning defined herein.

As used herein, the term “heteroatom” is meant to include oxygen (O), nitrogen (N), sulfur (S) and silicon (Si).

As used herein, the term “protecting group” refers to a substituent that is commonly employed to block or protect a particular functional group on a compound. For example, an “amino-protecting group” is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a “hydroxy-protecting group” refers to a substituent of a hydroxy group that blocks or protects the hydroxy functionality. Suitable protecting groups include acetyl and silyl. A “carboxy-protecting group” refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene’s Protective Groups in Organic Synthesis 4th edition, Wiley-Interscience New York, 2006.

As used herein a wavy line “∿” that intersects a bond in a chemical structure indicates the point of attachment of the bond that the wavy bond intersects in the chemical structure to the remainder of a molecule.

The compounds disclosed herein can also exist as tautomeric isomers. Although only one delocalized resonance structure may be depicted, all such forms are contemplated within the scope of the invention. For example, the imine and the keto-enamine shown below represent tautomeric isomers of the invention:

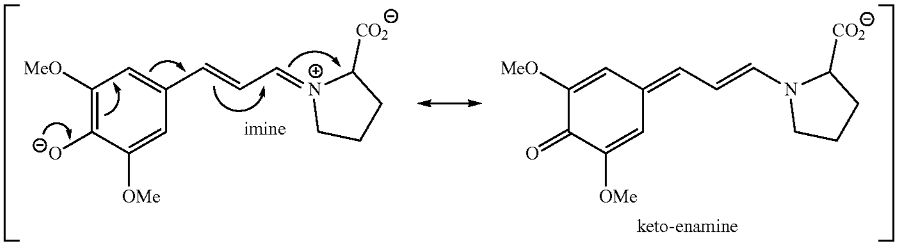

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a $—CH_3$ group may be substituted with $—CD_3$.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., “Stereochemistry of Organic Compounds”, John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms “racemic mixture” and “racemate” refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(═O)$NH_2$) or acetyl group). The open valence can also be created by the chemical conversion of a first function group of the compound to a second functional group of the compound (e.g., reduction of a carbonyl group, replacement of a carbonyl group with an amine), followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, Protecting Groups In Organic Synthesis; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term saccharide includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995. A saccharide can conveniently be linked to the remainder of a compound of formula I through an ether bond.

The term "chitosan" refers to a linear polysaccharide composed of randomly distributed β-linked D-glucosamine and N-acetyl-D-glucosamine. It is made by treating the chitin shells of shrimp and other crustaceans with an alkaline substance, like sodium hydroxide. Chitosan has a number of commercial and possible biomedical uses.

The term "ambient temperature" refers to the temperature of the surrounding medium, such as air or liquid, that comes into contact with the reaction mixture, device or apparatus.

The term "primary amine" refers to amines that only one of the hydrogen atoms in the ammonia molecule has been replaced. That means that the formula of the primary amine will be R—$NH_2$ where "R" is alkyl, aryl group etc.

The term "secondary amine" refers to amines that the two of the hydrogens in an ammonia molecule have been replaced by hydrocarbon groups.

The term "fiber" refers, for example, to a fine, threadlike piece, as of cotton, jute, or asbestos.

The term "buffer system (more precisely, pH buffer or hydrogen ion buffer)" refers to an aqueous solution consisting of a mixture of a weak acid and its conjugate base, or a weak base and its conjugate acid In one embodiment, a specific value for $R^1$ is 2-hydroxyphenyl, 4-nitrophenyl, 4-diethylaminophenyl, 3-methoxy-4-acetoxyphenyl, 3-methoxy-4-hydroxyphenyl and 3,5-dimethoxy-4-hydroxyphenyl.

In one embodiment, a specific value for $R^2$ is is residue of glucose, a residue of chitosan, a residue of His, a residue of Trp, H, s-butyl, t-butyl, carboxymethyl and tris(hydroxymethyl)methyl.

In one embodiment, a specific value for $R^3$ is s-butyl, carboxymethyl and tris(hydroxymethyl)methyl.

In one embodiment, a specific value for $R^2$ and $R^3$ together with the nitrogen to which they are attached is indolinyl, pyrrolidinyl, pyrrolinyl, prolinyl, 2-carboxypyrrolinyl, 4-hydroxyprolinyl, 2-methoxycarbonylpyrrolidinyl or 2-methoxycarbonylpyrrolinyl.

In one embodiment, the invention provides, a method comprising reacting a food or fiber that contains an amine with an aldehyde of formula 2:

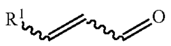

(2)

in the presence of a suitable base, such that the amine reacts with the aldehyde to provide a food or fiber that contains the corresponding imine or a salt thereof.

One embodiment provides a compound or a salt selected from:

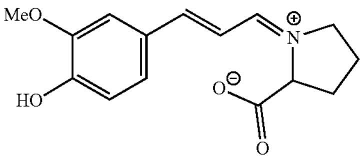

Z-isomer

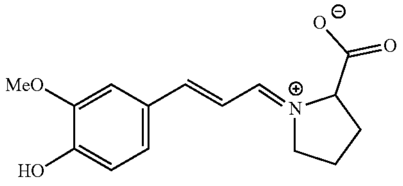

E-isomer

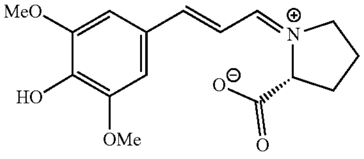

Z-isomer

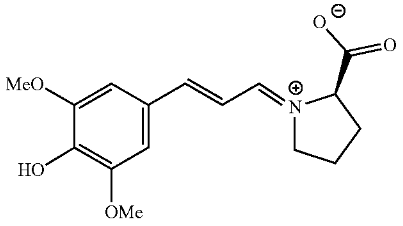

E-isomer

-continued

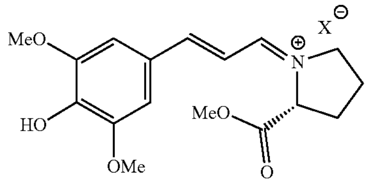

Z-isomer

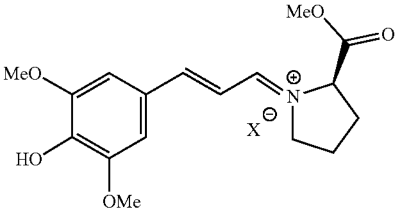

E-isomer

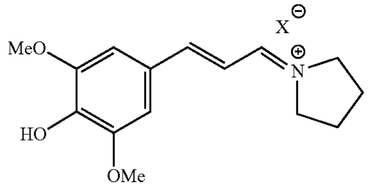

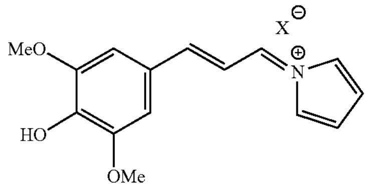

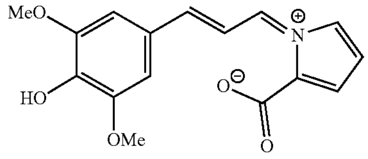

Z-isomer

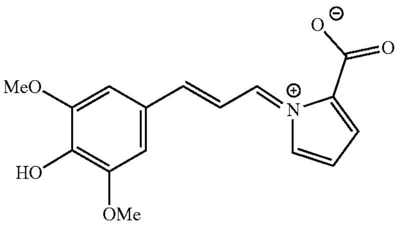

E-isomer

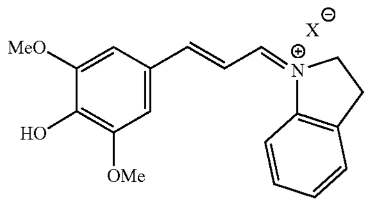

Z-isomer

-continued
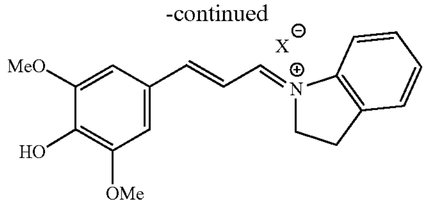
E-isomer
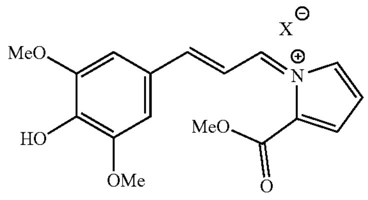
Z-isomer
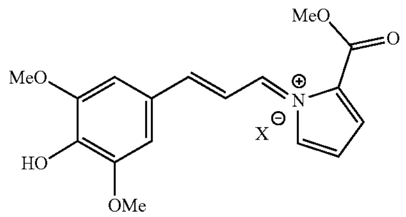
E-isomer
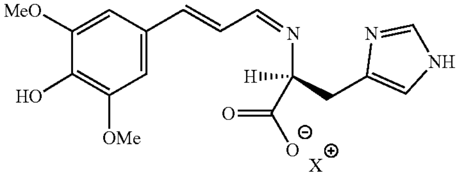
Z-isomer
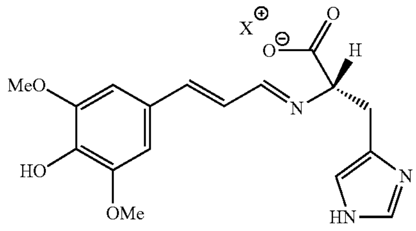
E-isomer
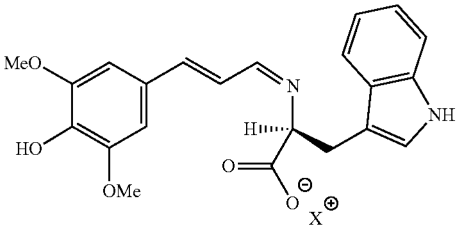
Z-isomer
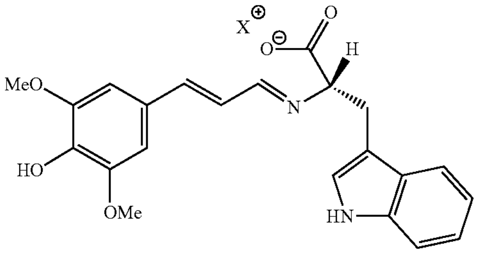
E-isomer
-continued
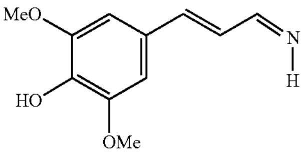
Z-isomer
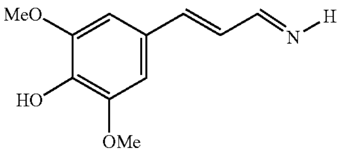
E-isomer
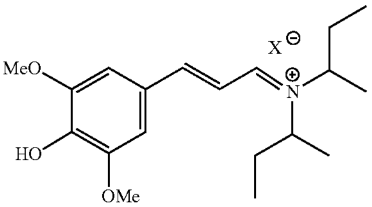
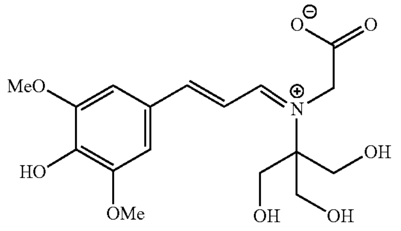
Z-isomer
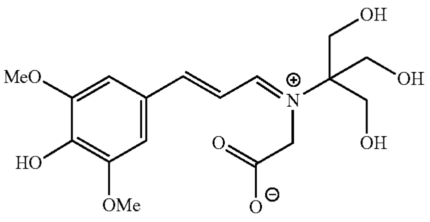
E-isomer
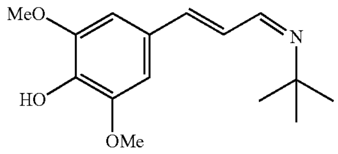
Z-isomer
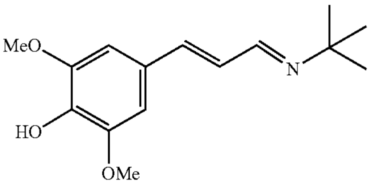
E-isomer
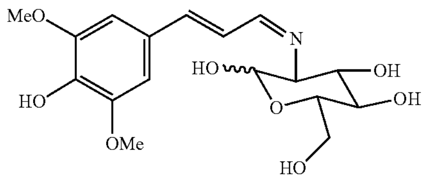
Z-isomer -continued

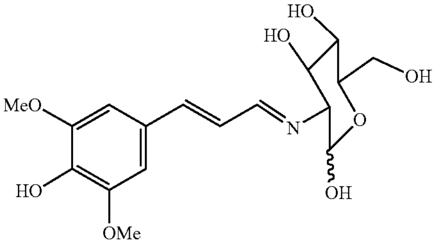

E-isomer

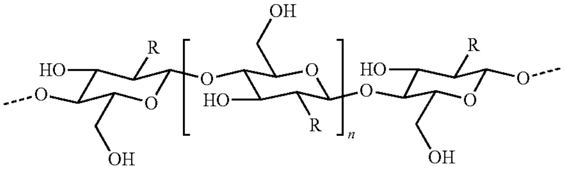

wherein n = 20 to 100

R = $NH_2$ or

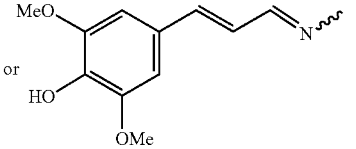

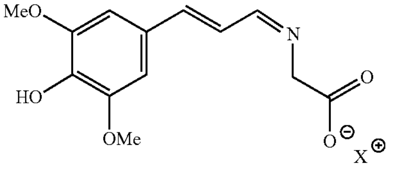

Z-isomer

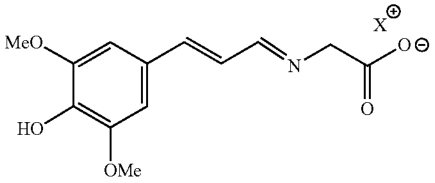

E-isomer

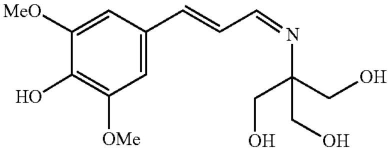

and

Z-isomer

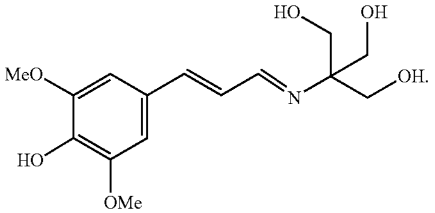

E-isomer

In one embodiment, the food comprises meat.

In one embodiment, the food comprises plant-based meat substitutes.

In one embodiment, the food comprises egg.

In one embodiment, the fiber comprises vegetable tissue.

In one embodiment, the fiber is a textile.

In one embodiment, the fiber comprises a mineral substance.

In one embodiment, the invention provides, a method to prepare a compound of formula (I), comprising:

reacting a corresponding aldehyde of formula 2:

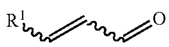

(2)

with a corresponding amine of formula 3:

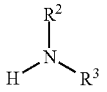

(3)

in the presence of a suitable base and in water, to provide the compound of formula (I), wherein the aldehyde of formula 2 is not reacted with the amine of formula 3 in a plant.

As described in the background, the floral nectar of *Nesocodon mauritianus* has a deep-red color that is attractive to its pollinators. This natural occurring alkaloid produced by the formation of an imine condensation product of sinapaldehyde and proline. Methods for synthesizing non-natural compounds with similar properties to the natural pigment in commercial scale are underdeveloped. Accordingly, in one embodiment the invention provides, a method to prepare a compound of formula (I), comprising:

reacting at least 1 gram of a corresponding aldehyde of formula 2:

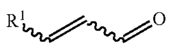

(2)

with a corresponding amine of formula 3:

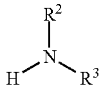

(3)

in the presence of a suitable base and in water, to provide the compound of formula (I).

In another embodiment, the invention provides, a method to prepare a compound of formula (I), comprising:

reacting at least 5 grams of a corresponding aldehyde of formula 2:

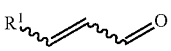

(2)

with a corresponding amine of formula 3:

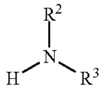

(3)

in the presence of a suitable base and in water, to provide the compound of formula (I).

In another embodiment, the invention provides, a method to prepare a compound of formula (I), comprising:

reacting at least 10 grams of a corresponding aldehyde of formula 2:

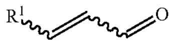

(2)

with a corresponding amine of formula 3:

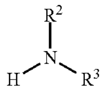

(3)

in the presence of a suitable base and in water, to provide the compound of formula (I).

In another embodiment, the invention provides, a method to prepare a compound of formula (I), comprising:

reacting a corresponding aldehyde of formula 2:

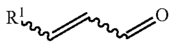

(2)

with at least 1 gram of a corresponding amine of formula 3:

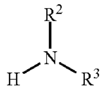

(3)

in the presence of a suitable base and in water, to provide the compound of formula (I).

In another embodiment, the invention provides, a method to prepare a compound of formula (I), comprising:

reacting a corresponding aldehyde of formula 2:

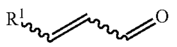

(2)

with at least 5 grams of a corresponding amine of formula 3:

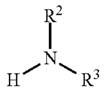

(3)

in the presence of a suitable base and in water, to provide the compound of formula (I).

In another embodiment, the invention provides, a method to prepare a compound of formula (I), comprising:

reacting a corresponding aldehyde of formula 2:

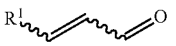

(2)

with at least 10 grams of a corresponding amine of formula 3:

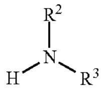

(3)

in the presence of a suitable base and in water, to provide the compound of formula (I).

In another embodiment, the invention provides, a method to prepare a compound of formula (I), comprising:

reacting a corresponding aldehyde of formula 2:

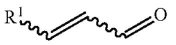

(2)

with a corresponding amine of formula 3:

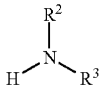

(3)

in the presence of a suitable base and in water, to provide at least 1 gram the compound of formula (I).

In another embodiment, the invention provides, a method to prepare a compound of formula (I), comprising:

reacting a corresponding aldehyde of formula 2:

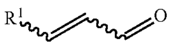

(2)

with a corresponding amine of formula 3:

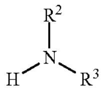

(3)

in the presence of a suitable base and in water, to provide at least 5 grams the compound of formula (I).

In another embodiment, the invention provides, a method to prepare a compound of formula (I), comprising:

reacting a corresponding aldehyde of formula 2:

(2)

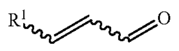

with a corresponding amine of formula 3:

(3)

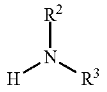

in the presence of a suitable base and in water, to provide at least 10 grams the compound of formula (I).

In one embodiment the commercial vessel has a volume of at least 1 liter. In one embodiment the commercial vessel has a volume of at least 2 liters. In one embodiment the commercial vessel has a volume of at least 5 liters. In one embodiment the commercial vessel has a volume of at least 10 liters.

In one embodiment, the reaction is performed in the presence of a polar solvent with less than 5% in water. In one embodiment, the reaction is performed in the presence of a polar solvent with less than 4% in water. In one embodiment, the reaction is performed in the presence of a polar solvent with less than 3% in water. In one embodiment, the reaction is performed in the presence of a polar solvent with less than 2% in water. In one embodiment, the reaction is performed in the presence of a polar solvent with less than 1% in water.

In one embodiment, the reaction is performed in the presence of a buffered aqueous system at a pH range of 6 to 9. In one embodiment, the reaction is performed in the presence of a buffered aqueous system at a pH range of 6 to 7. In one embodiment, the reaction is performed in the presence of a buffered aqueous system at a pH range of 6 to 8. In one embodiment, the reaction is performed in the presence of a buffered aqueous system at a pH range of 7 to 9. In one embodiment, the reaction is performed in the presence of a buffered aqueous system at a pH range of 8 to 9.

In one embodiment, the buffered aqueous system is a non-amine buffer.

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, the invention provides acid and base salts. Examples of salts include acid addition salts formed with acids, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. The invention also provides salts Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The invention will now be illustrated by the following non-limiting Examples.

EXAMPLES

Example 1. Synthesis of Nesocodin

Nescodonin was prepared by dissolving tsinapaldehyde in methanol at a concentration of 1-10 mM and then adding 1 molar equivalent of proline dissolved in methanol and a sub-stoichiometric quantity of a non-nucleophilic base catalyst (e.g. either triethylamine or tributylamine). A yellow to red color change was immediately observable and the reaction ran to completion within minutes to an hour at room temperature.

E/Z-Nesocodin Purification. Once the reaction was complete the contents of the reaction flask was diluted ten-fold into room temperature ethyl acetate. A red solid precipitate consisting of a roughly 1 to 2 mixture of Z- to E-isomers of nesocodin was collected by filtration, washed with a small volute of ice cold ethyl acetate and dried in vacuo overnight.

NMR of Synthetic Nesocodin. 600 MHz 1d $^{1}H$-NMR and $^{13}C$-NMR, and 2d DQF-COSY (Double Quantum Filtered COrrelation SpectroscopY) spectra were obtained for the synthesized 1 to 2 mixture of Z- and E-nesocodin isomers. Assignments are provided in Table 1 ($^{1}H$-NMR) and Table 2 ($^{13}C$-NMR). Data were obtained on a Bruker 600 MHz NMR at the Minnesota NMR Center on a fee for service basis.

Scheme 1. Structures of E and Z isomers of nesocodin with protons labeled A through L for assignment of $^{1}H$—NMR data

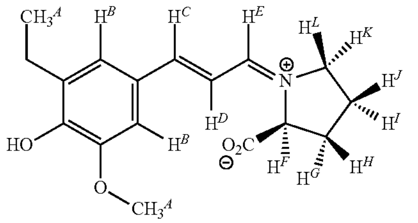

Z-isomer (36%)

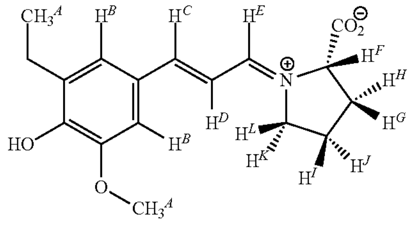

E-isomer (64%)

TABLE 1

| Summary of ID and 2D $^1$H-NMR resonances for both E and Z isomers of nesocodin (600 MHz) in methanol-$d_4$ | | |
|---|---|---|
| Proton(s) (isomer) | 1D $^1$H-NMR | DQF-COSY indicated couplings |
| $H^A$ (E) | δ 3.82 (s, 3H, $CH_3$) | none |
| $H^A$ (Z) | δ 3.80 (s, 3H, $CH_3$) | none |
| $H^B$ (E) | δ 6.99 (broad s, 2H) | none |
| $H^B$ (Z) | δ 6.92 (broad s, 2H) | none |
| $H^C$ (E) | δ 7.47 (d, 1H, J = 14 Hz) | δ 6.47 ($H^D$) |
| $H^C$ (Z) | δ 7.42 (d, 1H, J = 14 Hz) | δ 6.26 ($H^D$) |
| $H^D$ (E) | δ 6.47 (dd, 1H, J = 12, 14 Hz) | δ 7.83, 7.47 ($H^C$, $H^D$) |
| $H^D$ (Z) | δ 6.26 (dd, 1H, J = 12, 14 Hz) | δ 7.87, 7.42 ($H^C$, $H^D$) |
| $H^E$ (E) | δ 7.83 (d, 1H, J = 12 Hz) | δ 6.47, 4.41, 3.80, 3.70 ($H^D$, $H^F$, $H^K$, $H^L$) |
| $H^E$ (Z) | δ 7.87 (d, 1H, J = 12 Hz) | δ 6.26, 4.35, 3.94 ($H^D$, $H^H$, $H^L$) |
| $H^F$ (E) | δ 4.41 (dd, 1H, J = 5, 8 Hz) | δ 7.83, 2.31, 2.25 ($H^E$, $H^G$, $H^H$) |
| $H^F$ (Z) | δ 4.35 (dd, 1H, J = 5, 8 Hz) | δ 7.87, 2.44, 2.22 ($H^E$, $H^G$, $H^H$) |
| $H^G$ (E) | δ 2.31 (dq, 1H, J = 13, 8 Hz) | δ 4.41, 3.80, 3.70, 2.25 ($H^F$, $H^L$, $H^K$, $H^H$) |
| $H^G$ (Z) | δ 2.44 (dq, 1H, J = 13, 8 Hz) | δ 4.35, 3.94, 3.82, 2.22, 1.98 ($H^F$, $H^L$, $H^K$, $H^I$, $H^J$) |
| $H^H$ (E) | δ 2.25 (tt, 1H, J = 13, 7 Hz) | δ 4.41, 2.31, 2.05 ($H^F$, $H^G$, $H^{I, J}$) |
| $H^H$ (Z) | δ 2.22 (tt, 1H, J = 13, 7 Hz) | δ 4.35, 2.44, 2.09, 1.98 ($H^F$, $H^G$, $H^I$, $H^J$) |
| $H^{I, J}$ (E) | δ 2.05 (m, 2H) | δ 3.80, 3.70, 2.25 ($H^L$, $H^K$, $H^H$) |
| $H^I$ (Z) | δ 2.09 (m, 2H) | δ 3.94, 3.82, 2.22, 1.98 ($H^L$, $H^K$, $H^H$, $H^J$) |
| $H^J$ (Z) | δ 1.98 (tq, 1H, 12, 7) | δ 3.94, 3.82, 2.44, 2.22, 2.09 ($H^L$, $H^K$, $H^G$, $H^H$, $H^I$) |
| $H^K$ (E) | δ 3.70 (dt, 1H, J = 13, 8 Hz) | δ 3.80, 2.05 ($H^L$, $H^{I, J}$) |
| $H^K$ (Z) | δ 3.82 (dt, 1H, J = 12, 7 Hz) | δ 3.94, 2.09, 1.98 ($H^L$, $H^I$, $H^J$) |
| $H^L$ (E) | δ 3.80 (dt, 1H, J = 13, 8 Hz) | δ 3.70, 2.05 ($H^K$, $H^{I, J}$) |
| $H^L$ (Z) | δ 3.94 (dt, 1H, J = 12, 7 Hz) | δ 3.82, 2.09, 1.98 ($H^K$, $H^I$, $H^J$) |

Scheme 2. Structures of nesocodin with carbons labeled 1 through 13 for assignment of $^{13}$C—NMR data.

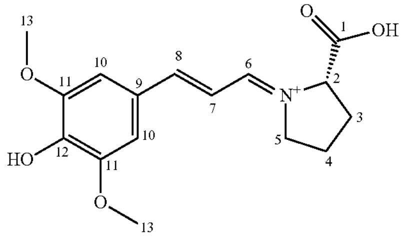

E-isomer
(Z-isomer not shown)

TABLE 2

| Summary of ID $^{13}$C-NMR resonances for both E and Z isomers of nesocodin (600 MHz) in methanol-$d_4$ | | |
|---|---|---|
| Proton(s) (isomer) | 1D $^{13}$C-NMR proton decoupled | 1D $^{13}$C-NMR proton coupling |
| $C^1$ (E) | δ 176.78 | d, 4 Hz |
| $C^1$ (Z) | δ 176.90 | d, 4 Hz |
| $C^2$ (E) | δ 70.19 | dt, 146, 4 Hz |
| $C^2$ (Z) | δ 66.16 | dt, 146, 4 Hz |
| $C^3$ (E) | δ 31.46 | tq, 131, 4 Hz |
| $C^3$ (Z) | δ 32.34 | tq, 131, 4 Hz |
| $C^4$ (E) | δ 24.76 | tm, 132, 4 Hz |
| $C^4$ (Z) | δ 24.94 | tm, 132, 4 Hz |
| $C^5$ (E) | δ 50.60 | tt, 143, 4 Hz |
| $C^5$ (Z) | δ 56.08 | tt, 140, 4 Hz |
| $C^6$ (E) | δ 160.57 | dd, 172, 7 Hz |
| $C^6$ (Z) | δ 160.52 | dd, 172, 7 Hz |
| $C^7$ (E) | δ 159.27 | dt, 151, 5 Hz |
| $C^7$ (Z) | δ 159.22 | dt, 151, 5 Hz |
| $C^8$ (E) | δ 159.83 | dd, 151, 5 Hz |
| $C^8$ (Z) | δ 159.77 | dd, 151, 5 Hz |
| $C^9$ (E) | δ 166.63 | t, 6 Hz |

TABLE 2-continued

| Summary of ID $^{13}$C-NMR resonances for both E and Z isomers of nesocodin (600 MHz) in methanol-$d_4$ | | |
|---|---|---|
| Proton(s) (isomer) | 1D $^{13}$C-NMR proton decoupled | 1D $^{13}$C-NMR proton coupling |
| $C^9$ (Z) | δ 167.11 | t, 6 Hz |
| $C^{10}$ (E) | δ 106.20 | dd, 158, 3 Hz |
| $C^{10}$ (Z) | δ 106.01 | dd, 158, 3 Hz |
| $C^{11}$ (E) | δ 118.76 | d, 4 Hz |
| $C^{11}$ (Z) | δ 118.66 | d, 4 Hz |
| $C^{12}$ (E) | δ 161.52 | s |
| $C^{12}$ (Z) | δ 161.49 | s |
| $C^{13}$ (E) | δ 56.22 | q, 143.7 Hz |
| $C^{13}$ (Z) | δ 56.20 | q, 143.7 HZ |

Comparison of Synthetic Nesocodin to *Nesocodon* Inflorescence Derived Red Pigment.

UV/Vis spectra, UHPLC C18 reverse phase retention time, exact mass and MS/MS fragmentation patterns are indistinguishable between the flower-derived and synthetic 1 to 2 mixture of Z- and E-nesocodin isomers. The floral pigment also appears to exist as a 1:2 mixture of Z- and E-isomers based on the presence of two closely eluting peaks in the LC-MS analysis. This would be expected if the proline/sinapaldehyde reaction is non-enzymatic but occurs spontaneously as the pH increases during nectar maturation.

A procedure similar to that described in Example 1 can be used to prepare other compounds of formula (I).

Example 2. LC-HRMS Analysis

Chromatographic separation and high-resolution mass spectral analysis were performed using a UHPLC coupled to a hybrid quadrupole-Orbitrap mass spectrometer (Ultimate® 3000 HPLC, Q Exactive™, Thermo Scientific). The UHPLC is equipped with a flow-through Photo Diode Array (PDA) detector allowing concurrent UV/visible spectrophotometric and MS analysis of separated analytes post-column. Samples were first purified by $C_{18}$ solid phase extraction using a Ziptip (Millipore) conditioned in ~20 μL of acetonitrile, washed with 20 μL of 0.1% formic acid in water, loaded with ~20 μL of nectar and washed with ~100 μL of 0.1% formic acid in water prior to elution with ~10 μL of acetonitrile. The eluate was then transferred into LC-MS autosampler vials and 1 μL was injected (via autosampler) onto a reversed-phase $C_{18}$ HSS $T_3$ 1.8 μm particle size, 2.1×100 mm column (Waters). Column temperature was 40° C. and solvent flow rate 0.45 mL/min. A 20-minute linear gradient using mobile phases A: 0.1% formic acid in water and B: 0.1% formic acid in acetonitrile was run according to the following gradient 25 minute elution profile: initial, 2% B; 20 min, 98% B; 21 min, 98% B; 22 min, 2% B (hold to 25 min). The following MS conditions were used: full scan mass scan range: 100-1000 m/z, resolution: 70,000, data type: profile, desolvation temperature 350° C., capillary voltage: 3800 V (+), 4000 V (−). Xcalibur™ software version 2.1 (Thermo Scientific) was used to record and visualize the chromatograms and spectra.

Example 3. Red Chitosan/Sinapaldehyde Conjugate Biofilm Synthesis

Chitosan was dissolved/suspended in 1% acetic acid in water and ~1 amino equivalent of sinapaldehyde dissolved in methanol was added dropwise with stirring forming a yellow emulsion. The emulsion was allowed to dry in a shallow glass dish placed in an oven at 42° C. for 48 hours and produced a red film.

Example 4

Figure 1C:
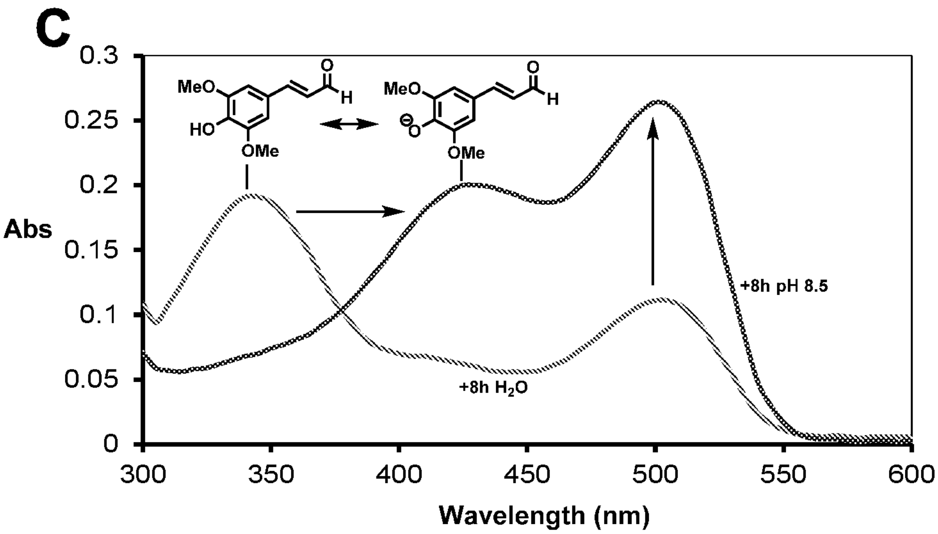

Absorbance spectra and pH of nectar was collected at 0, +8 hours and +24 hours. FIGS. 1A-1C show the results. (A) Absorbance spectra of nectars collected at 0 hour (yellow), +8 h (orange) and +24 hours (red) after dilution at 1:50 in $diH_2O$. Images of each non-diluted nectar and pH are noted in the inset. (B) Absorbance spectra of 0 h nectar after either being diluted in $diH_2O$ or 50 mM Tricine, pH 8.5. The red arrowhead indicates the location (505 nm) of the predominant peak present in +24 hours nectar. (C) Absorbance spectra of +8 h nectar after either being diluted in $diH_2O$ or 50 mM Tricine, pH 8.5.

Example 5

Figure 2A:
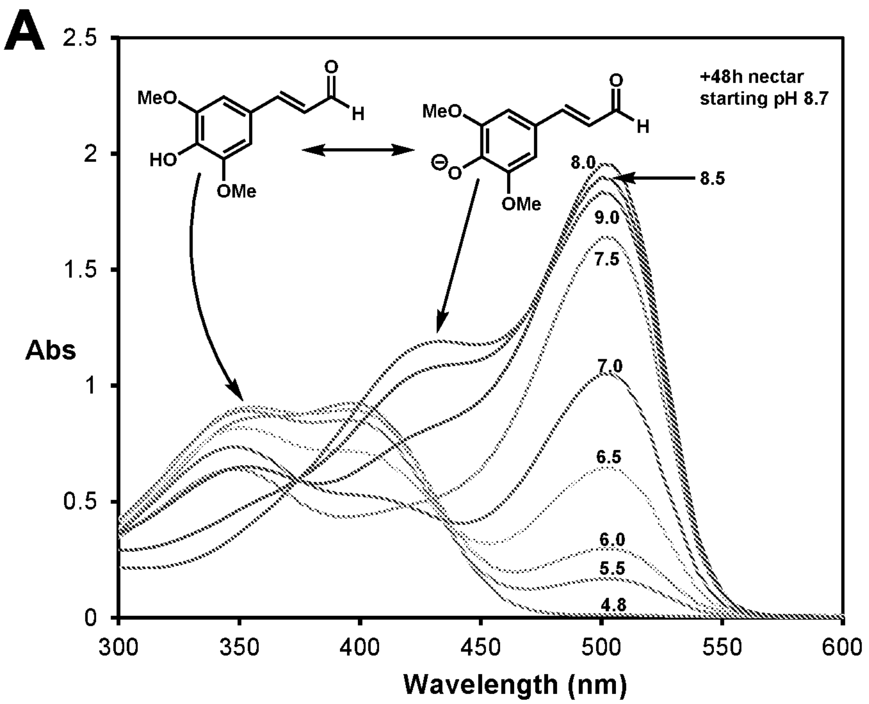
FIGS. 2A-2C show alkaline conditions are required for red nectar pigment intensity and stability. (A) Absorbance spectra of +48 hours (red) nectar as a function of pH. The absorbance spectra of raw red nectar (+48 hours) diluted 1:20 in 50 mM buffers at of varying pH, including: 4.8 (sodium acetate), 5.5 (MES), 6.0 (MES), 6.5 (MES), 7.0 (HEPES), 7.5 (HEPES), 8.0 (HEPES), 8.5 (Tricine), and 9.0 (TAPS). The inset shows the appearance of the diluted nectar at each pH. (B) The color change from red to yellow (e.g. from A) is reversible if the pH is returned to alkaline after a short period. Alkaline red nectar (+24 hours) was diluted 1:19 with 50 mM MES, pH 6.5 and immediately diluted again 1:4 in either $diH_2O$ or 100 mM Tricine, pH 8.5 (i.e., 20 ml of sample in 80 ml buffer) and subjected to UV-Vis spectrophotometric analysis. Samples similarly diluted stepwise in either $diH_2O$ or 50 mM Tricine, pH 8.5 were included as controls. (C) Red (+24 hours) nectar was diluted 1:1 with either 100 mM MES, pH 6.5 or 100 mM Tricine, pH 8.5 and incubated in the dark at 21° C. for 14 hours. The samples were further diluted 1:19 with 100 mM Tricine, pH 8.5 (i.e., 5 ml of sample into 95 ml buffer) and subjected to UV-Vis spectrophotometric analysis.
Figure 2B:
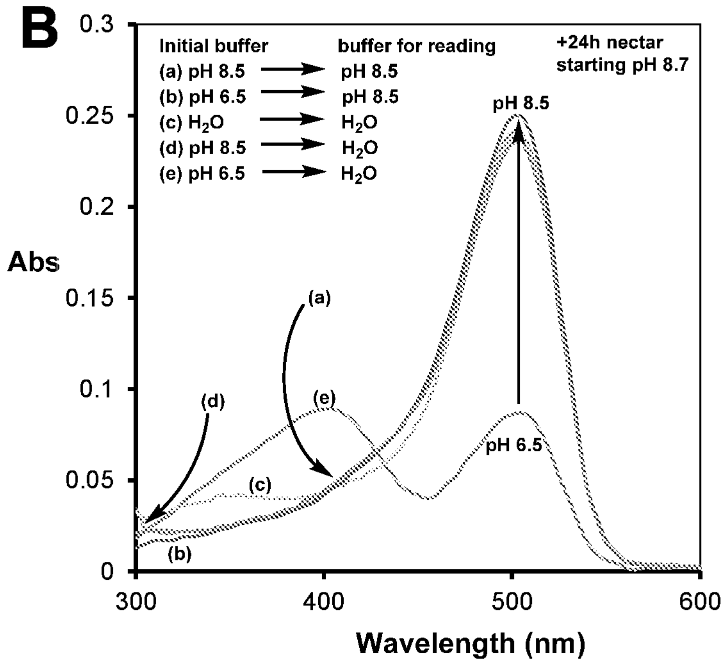
Figure 2C:
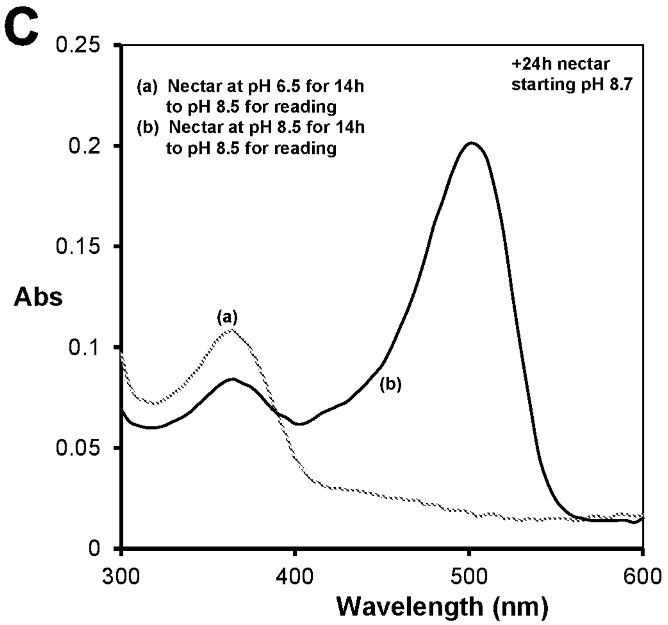
Figure 3A:
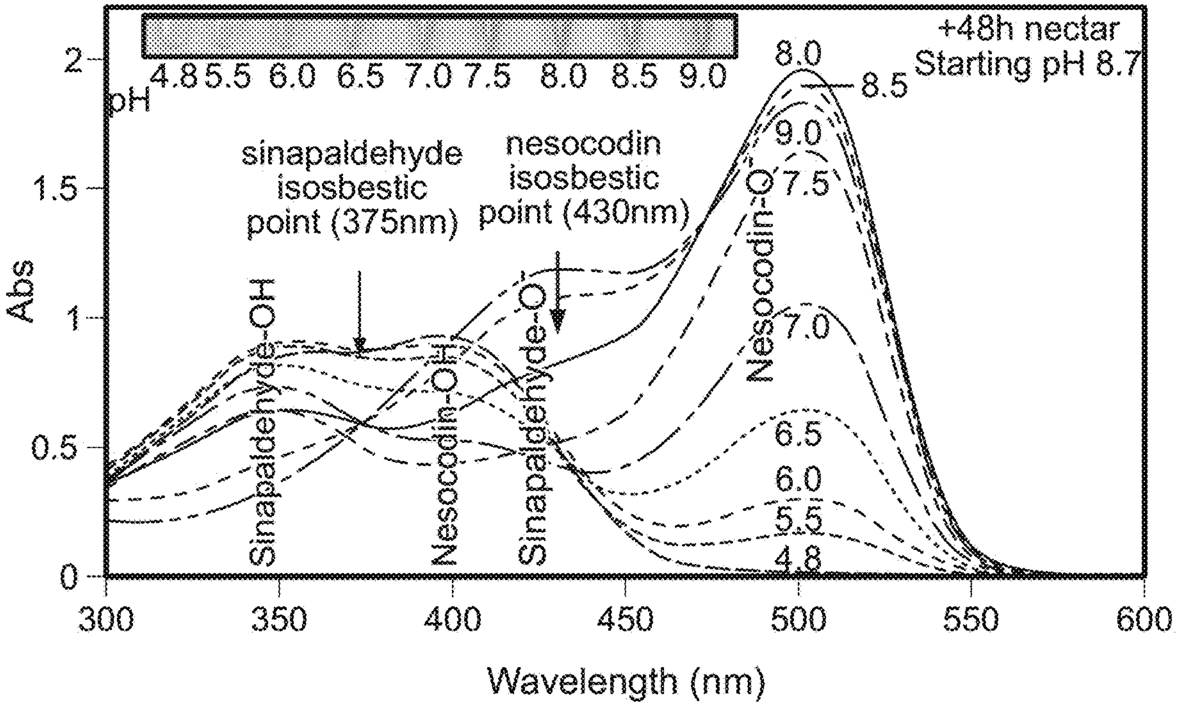
FIGS. 3A-3D show the changes in UV/visible spectra of red *Nesocodon* nectar (+48 hours nectar starting at unbuffered pH=8.7)) as the pH is varied by addition to buffer ranging in pH from 4.8 to 9.0. Panel A shows a pile up of the UV/visible spectra from 300 nm to 600 nm at pHs 4.8, 5.5, 6.0, 6.5, 7.0, 7.5, 8.0, 8.5 and 9.0. Isosbestic points are apparent at 375 nm for the protonation/deprotonation of sinapaldehyde and 430 for the protonation/deprotonation of nesocodin. Panel B shows a plot of the absorbance at these isosbestic points normalized to range between 1 and 0. By observing the spectral changes at the isosbestic points it is possible to remove the pH dependent contributions from the overlapping chromophores. The nesocodin $pK_A$ can be measured at the sinapaldehyde isosbestic point by following the pH dependent decrease in the protonated nesocodin as the pH increases, and the sinapaldehyde pKa can be measured at the nesocodin isosbestic point by following the pH dependent increase in the deprotonated sinapaldehyde as the pH increases. Using this approach the nesocodin appears to have a $pK_A$ of 6.5 and the sinapaldehyde has a $pK_A$ of 8.0. The lower $pK_A$ for nesocodin is consistent with the added resonance delocalization of the phenolate negative charge through the conjugated system to the positively charged imino functionality as shown in panel C. Panel D shows the conjugate acid/base equilibrium for sinapaldehyde.
Figure 3B:
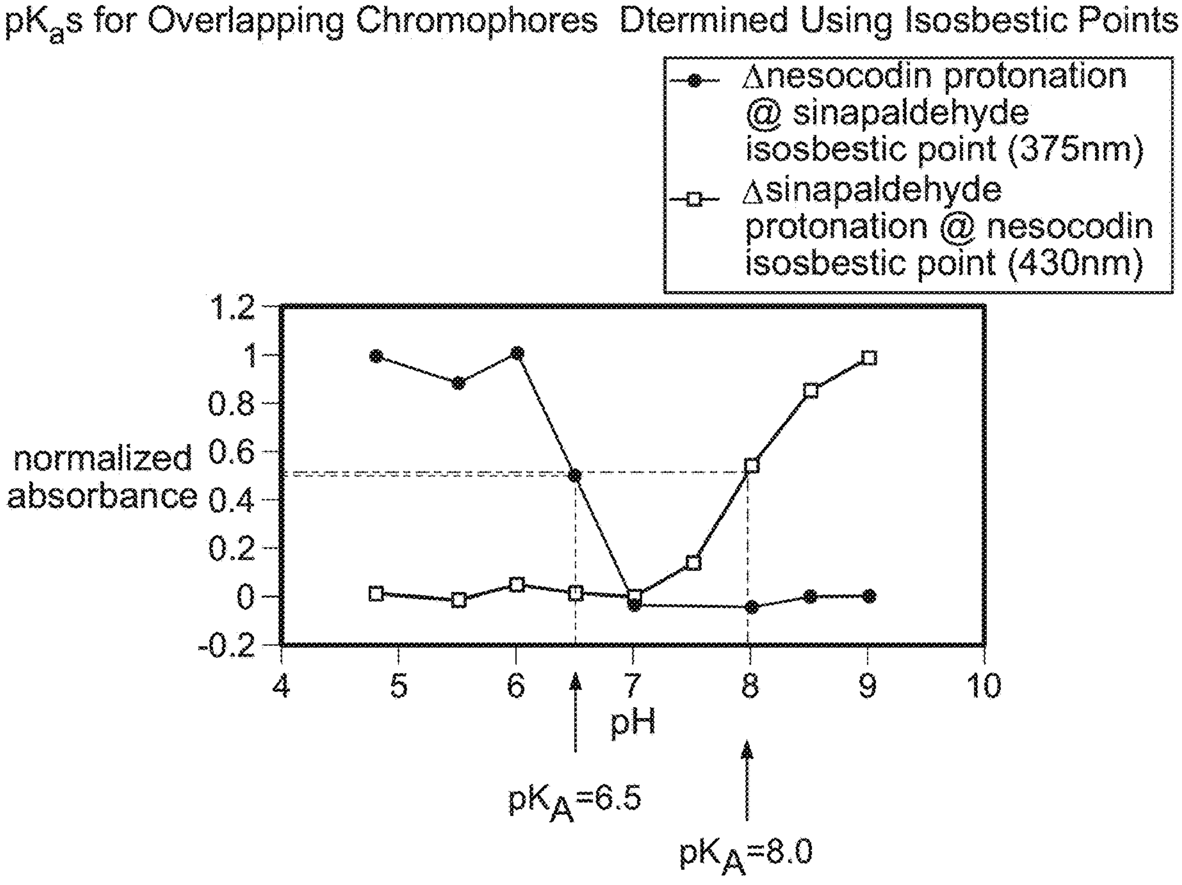
Figure 3C:
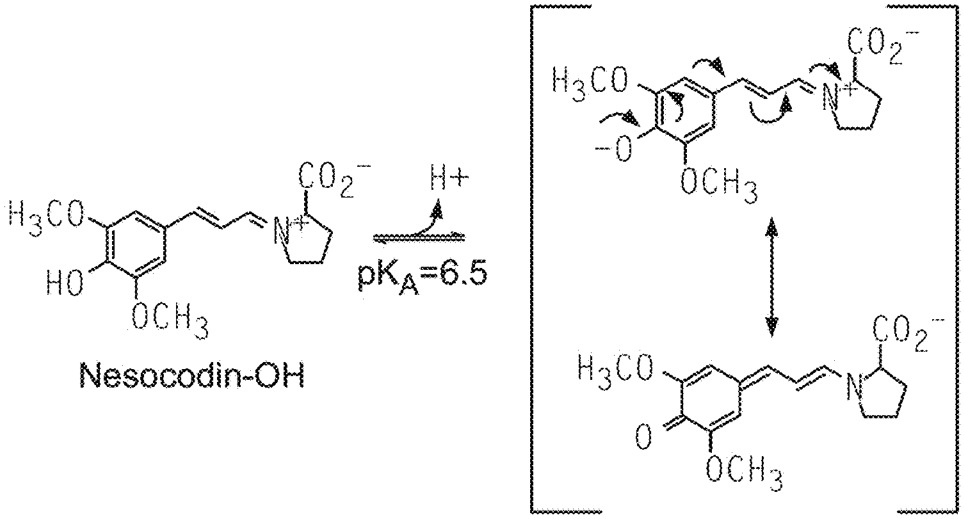
Figure 3D:
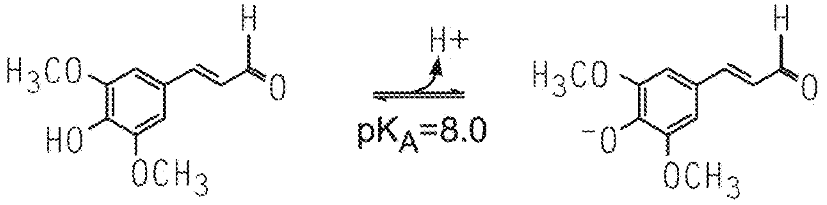

As shown in FIGS. 2A-2C, it was determined that alkaline conditions are required for red nectar pigment intensity and stability. (A) Absorbance spectra of +48 hours (red) nectar as a function of pH. The absorbance spectra of raw red nectar (+48 hours) diluted 1:20 in 50 mM buffers at of varying pH, including: 4.8 (sodium acetate), 5.5 (MES), 6.0 (MES), 6.5 (MES), 7.0 (HEPES), 7.5 (HEPES), 8.0 (HEPES), 8.5 (Tricine), and 9.0 (TAPS). The inset shows the appearance of the diluted nectar at each pH. (B) The color change from red to yellow (e.g. from A) is reversible if the pH is returned to alkaline after a short period. Alkaline red nectar (+24 hours) was diluted 1:19 with 50 mM MES, pH 6.5 and immediately diluted again 1:4 in either $diH_2O$ or 100 mM Tricine, pH 8.5 (i.e., 20 ml of sample in 80 ml buffer) and subjected to UV-Vis spectrophotometric analysis. Samples similarly diluted stepwise in either $diH_2O$ or 50 mM Tricine, pH 8.5 were included as controls. (C) Red (+24 hours) nectar was diluted 1:1 with either 100 mM MES, pH 6.5 or 100 mM Tricine, pH 8.5 and incubated in the dark at 21° C. for 14 hours. The samples were further diluted 1:19 with 100 mM Tricine, pH 8.5 (i.e., 5 ml of sample into 95 ml buffer) and subjected to UV-Vis spectrophotometric analysis.

Example 6

As shown in FIGS. 3A-3D the changes in UV/visible spectra of red *Nesocodon* nectar (+48 hours nectar starting at unbuffered pH=8.7)) as the pH is varied by addition to buffer ranging in pH from 4.8 to 9.0 was measured. Panel A shows a pile up of the UV/visible spectra from 300 nm to 600 nm at pHs 4.8, 5.5, 6.0, 6.5, 7.0, 7.5, 8.0, 8.5 and 9.0. Isosbestic points are apparent at 375 nm for the protonation/deprotonation of sinapaldehyde and 430 for the protonation/deprotonation of nesocodin. Panel B shows a plot of the absorbance at these isosbestic points normalized to range between 1 and 0. By observing the spectral changes at the isosbestic points it is possible to remove the pH dependent contributions from the overlapping chromophores. The nesocodin $pK_A$ can be measured at the sinapaldehyde isosbestic point by following the pH dependent decrease in the protonated nesocodin as the pH increases, and the sinapaldehyde pKa can be measured at the nesocodin isosbestic point by following the pH dependent increase in the deprotonated sinapaldehyde as the pH increases. Using this approach the nesocodin appears to have a $pK_A$ of 6.5 and the sinapaldehyde has a $pK_A$ of 8.0. The lower $pK_A$ for nesocodin is consistent with the added resonance delocalization of the phenolate negative charge through the conjugated system to the positively charged imino functionality as shown in panel C. Panel D shows the conjugate acid/base equilibrium for sinapaldehyde.

Example 7

Figure 4:
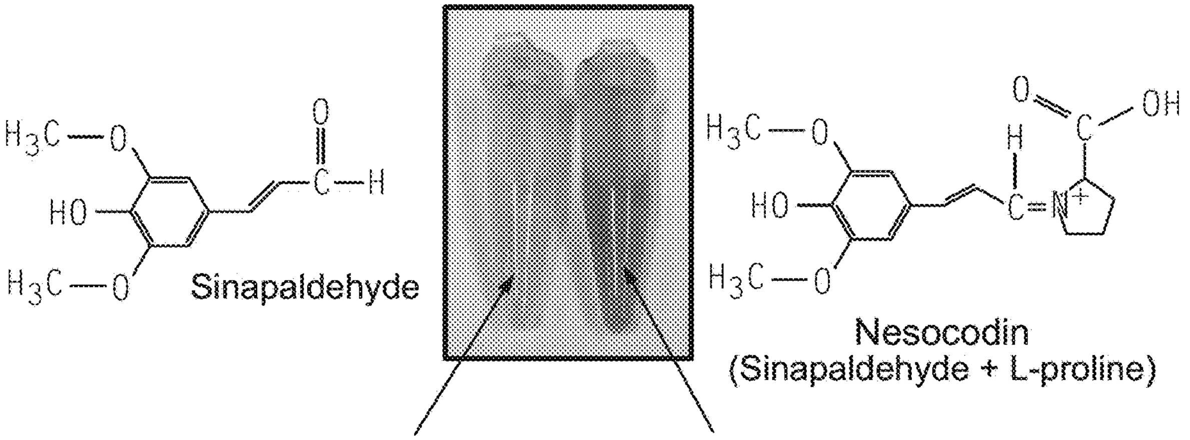
FIG. 4 shows organic synthesis of nesocodin in aqueous solution. 1 mM sinapaldehyde was incubated in 50 mM $NaHCO_3$ buffer at pH 9 either without (left) or with (right) 10 mM L-proline for 30 minutes at 22° C.
Figure 5:
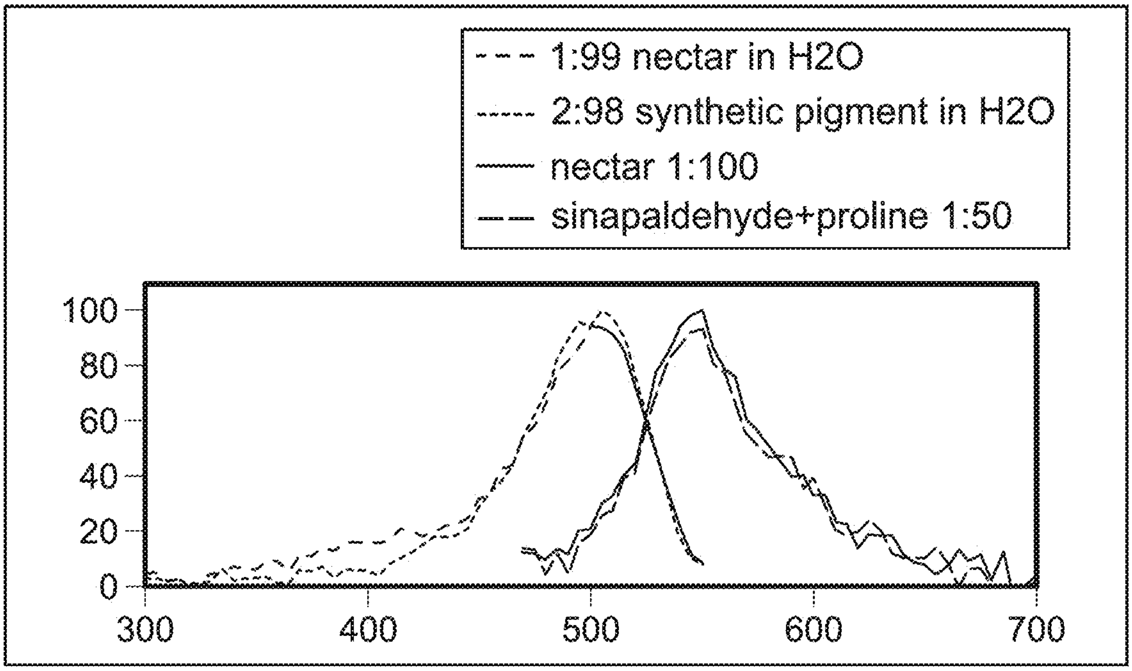
FIG. 5 shows validation of nesocodin pigment synthesis via (A) excitation and emission spectra of synthetic nesocodin (sinapaldehyde+proline, from FIG. 4) and raw nectar, both diluted 1:99 in 25 mM HEPES, pH 8.0 (B) thin-layer chromatography of synthetic nesocodin (sinapaldehyde+proline) and raw nectar (2 μl of each was spotted onto a silica gel TLC plate with a mobile phase of 100 mM sodium acetate, pH 4.8).

Nesocodin was synthesized in aqueous solution by incubating 1 mM sinapaldehyde in 50 mM $NaHCO_3$ buffer at pH 9 either without (left) or with (right) 10 mM L-proline for 30 minutes at 22° C. (See FIG. 4). FIG. 5 shows validation of nesocodin pigment synthesis via (A) excitation and emission spectra of synthetic nesocodin (sinapaldehyde+proline, from FIG. 4 and raw nectar, both diluted 1:99 in 25 mM HEPES, pH 8.0 (B) thin-layer chromatography of synthetic nesocodin (sinapaldehyde+proline) and raw nectar (2 μl of each was spotted onto a silica gel TLC plate with a mobile phase of 100 mM sodium acetate, pH 4.8).

Example 8

Figure 6:
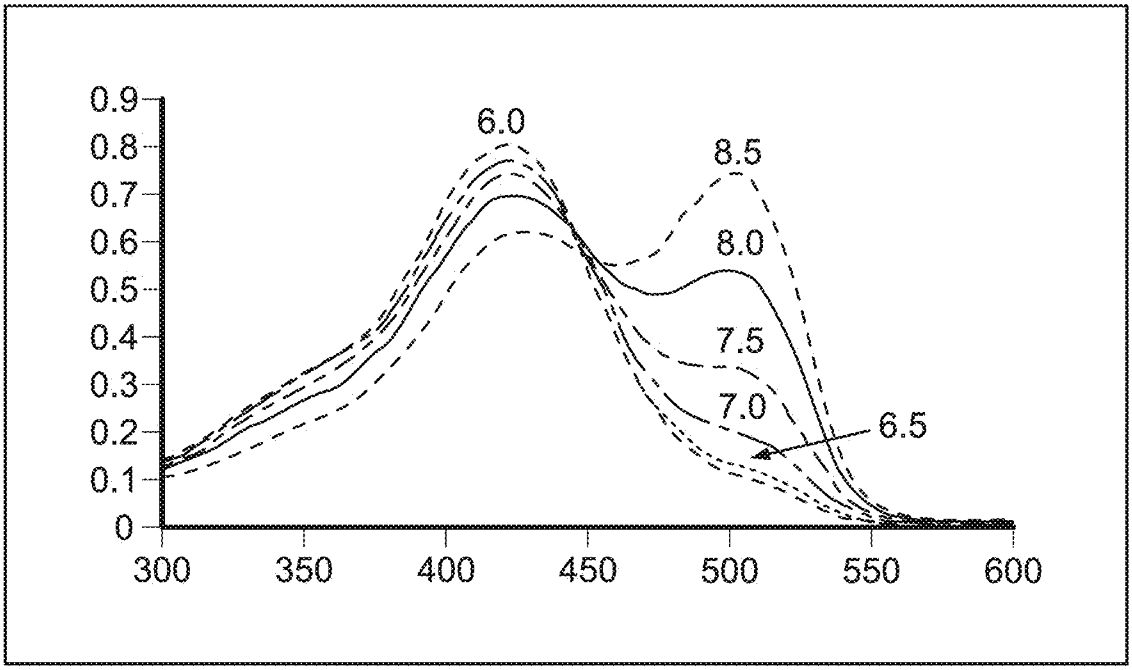
FIG. 6 shows top panels: pH-dependent formation of colored products between 1 mM sinapaldehyde and 10 mM proline in 25 mM buffers of varying pH, including 6.0 (MES), 6.5 (MES), 7.0 (HEPES), 7.5 (HEPES), 8.0 (HEPES), and 8.5 (Tricine). Bottom: Absorbance spectra of the reactions from the top panels after adjustment to pH 8.5 via 1:1 dilution with 100 mM Tricine, pH 8.5.

The pH-dependent formation of colored products between 1 mM sinapaldehyde and 10 mM proline was evaluated in 25 mM buffers of varying pH, including 6.0 (MES), 6.5 (MES), 7.0 (HEPES), 7.5 (HEPES), 8.0 (HEPES), and 8.5 (Tricine). The absorbance spectra of each reaction after adjustment to pH 8.5 via 1:1 dilution with 100 mM Tricine, pH 8.5 is shown in FIG. 6.

Example 9

Proline conjugates were formed in aqueous solution at 21° C. In each case 1 mM sinapaldehyde in 50 mM $NaHCO_3$, pH 9.0 was incubated with 10 mM of either L-proline, D-proline, 4-hydroxyproline (4-OH-L-proline), L-proline methyl ester or pyrrolidine. A color change demonstrated the formation of the respective conjugates.

Example 10

1 mM sinapaldehyde in 50 mM $Na(H)CO_3$, pH 9.0 was incubated with either 10 mM L-proline, 10 mM L-tryptophan, or 10 mM L-histidine at 21° C. for 1 hour. Pigment formation was specific to proline at 21° C. in aqueous solution.

Example 11

1 mM sinapaldehyde was boiled in 50 mM Tricine, at pH 8.5 for 5 minutes. The formation of a red color evidenced conjugate formation with the secondary amine Tricine.

Example 12

1d $^{13}$C-NMR spectrum in methanol-$d_4$ and LC-PDA data demonstrated that E- and Z nesocodin-isomers are present in about a 64 to 36 (nearly 2 to 1) ratio (respectively) when produced synthetically or when isolated from nectar.

Example 13

Figure 7:
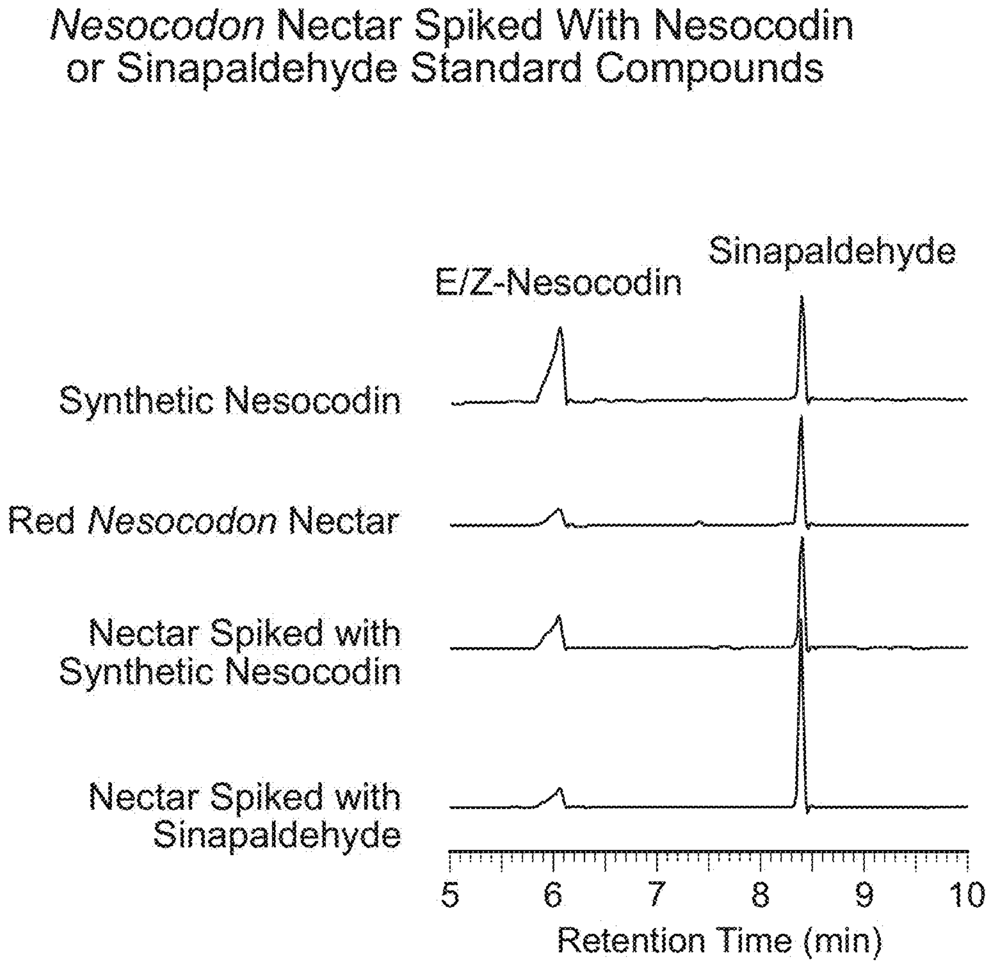
FIG. 7 shows portions (from retention times of 5 to 10 min) of separate LC-PDA analyses of 1) synthetic nesocodin, 2) red *nesocodon* nectar, 3) nectar spiked with synthetic nesocodin, and 4) nectar spiked with sinapaldehyde. This demonstrates the identical chromatographic behavior of the nesocodin and sinapaldehyde in the nectar with known standard compounds.

FIG. 7 shows portions (from retention times of 5 to 10 min) of separate LC-PDA analyses of 1) synthetic nesocodin, 2) red *nesocodon* nectar, 3) nectar spiked with synthetic nesocodin, and 4) nectar spiked with sinapaldehyde. The results show identical chromatographic behavior of the nesocodin and sinapaldehyde in the nectar with known standard compounds.

Example 14

Figure 8:
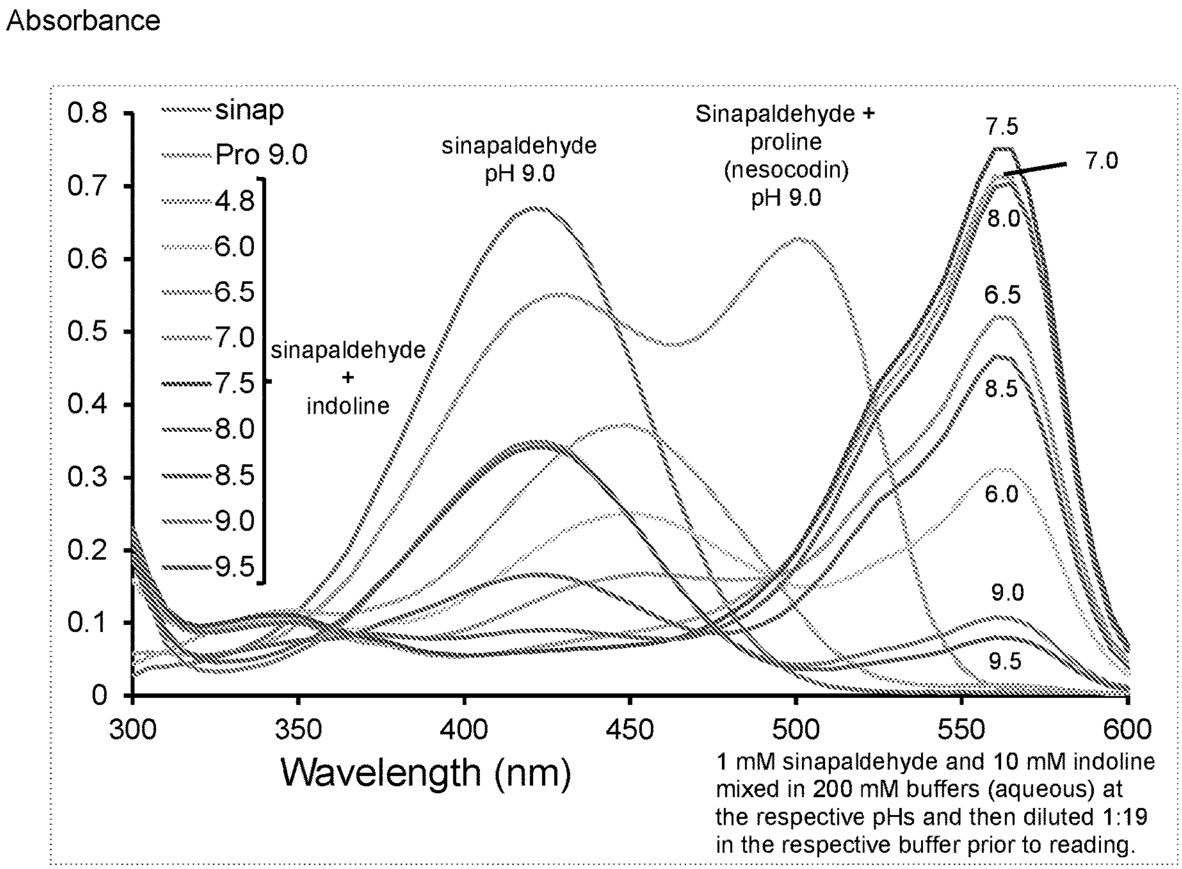
FIG. 8 shows the UV/Visible absorbance spectra of the different products from Example 14 after dilution 1:19 in 200 mM buffers of the same pH as used for synthesis, including: 4.8 (sodium acetate), 5.5 (MES), 6.0 (MES), 6.5 (MES), 7.0 (HEPES), 7.5 (HEPES), 8.0 (HEPES), 8.5 (Tricine), and 9.0 (sodium (bi)carbonate) and 9.5 (TAPS).

1 mM Sinapaldehyde was condensed with 10 mM indoline in 50 mM aqueous buffers of varying pH, including: 4.8 (sodium acetate), 5.5 (MES), 6.0 (MES), 6.5 (MES), 7.0 (HEPES), 7.5 (HEPES), 8.0 (HEPES), 8.5 (Tricine), 9.0 (sodium (bi)carbonate) and 9.5 (TAPS). The products formed were analyzed after a 1 hour incubation at 21° C. The UV/Visible absorbance spectra of the different products after dilution 1:19 in 200 mM buffers of the same pH as used for synthesis, including: 4.8 (sodium acetate), 5.5 (MES), 6.0 (MES), 6.5 (MES), 7.0 (HEPES), 7.5 (HEPES), 8.0 (HEPES), 8.5 (Tricine), and 9.0 (sodium (bi)carbonate) and 9.5 (TAPS) are shown in FIG. 8.

Example 15

Figure 9:
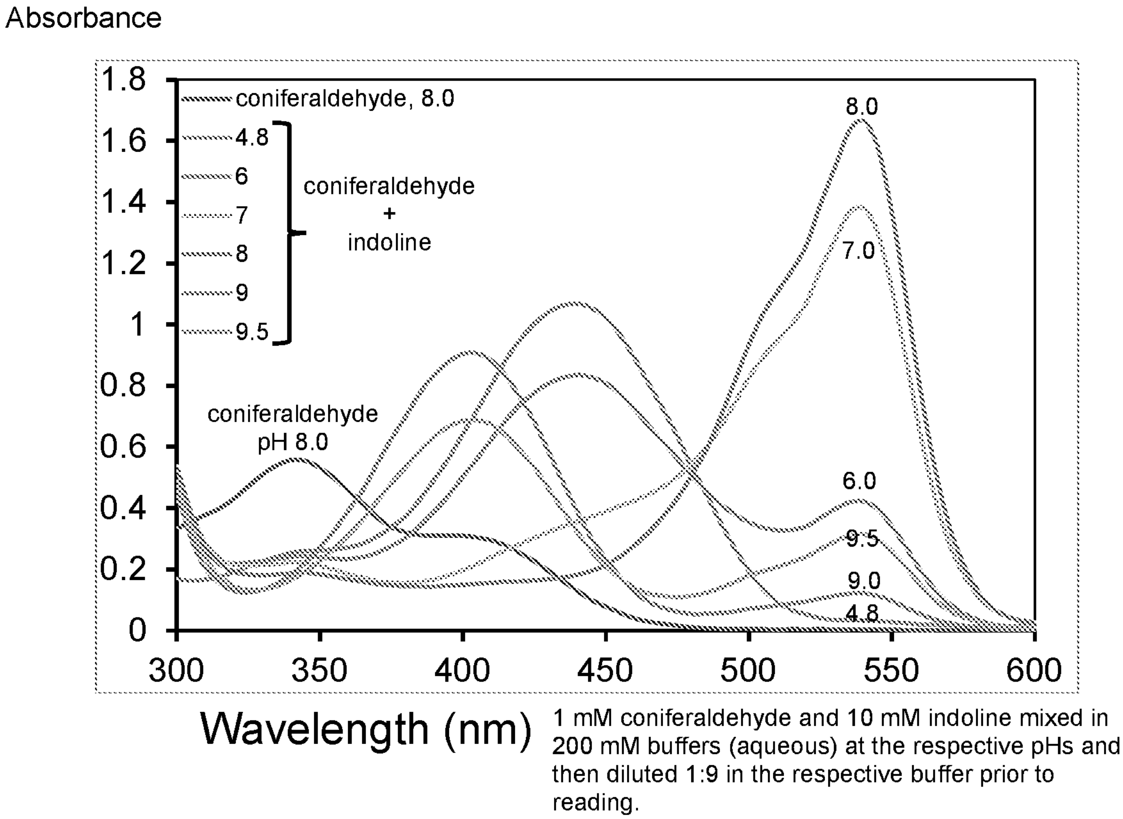
FIG. 9 shows the UV/Visible absorbance spectra of the different products from Example 15 after dilution 1:19 in 200 mM buffers of the same pH as used for synthesis, including: 4.8 (sodium acetate), 6.0 (MES), 7.0 (HEPES), 8.0 (HEPES), 9.0 (sodium (bi)carbonate), and 9.5 (TAPS).

1 mM Coniferaldehyde (4-hydroxy-3-methoxycinnamaldehyde) was condensed with 10 mM indoline in aqueous solutions of different pH, including 4.8 (sodium acetate), 6.0 (MES), 7.0 (HEPES), 8.0 (HEPES), 9.0 (sodium (bi)carbonate) and 9.5 (TAPS). The UV/Visible absorbance spectra of the different products after dilution 1:19 in 200 mM buffers of the same pH as used for synthesis, including: 4.8 (sodium acetate), 6.0 (MES), 7.0 (HEPES), 8.0 (HEPES), 9.0 (sodium (bi)carbonate), and 9.5 (TAPS) are shown in FIG. 9.

Example 16

Figure 10:
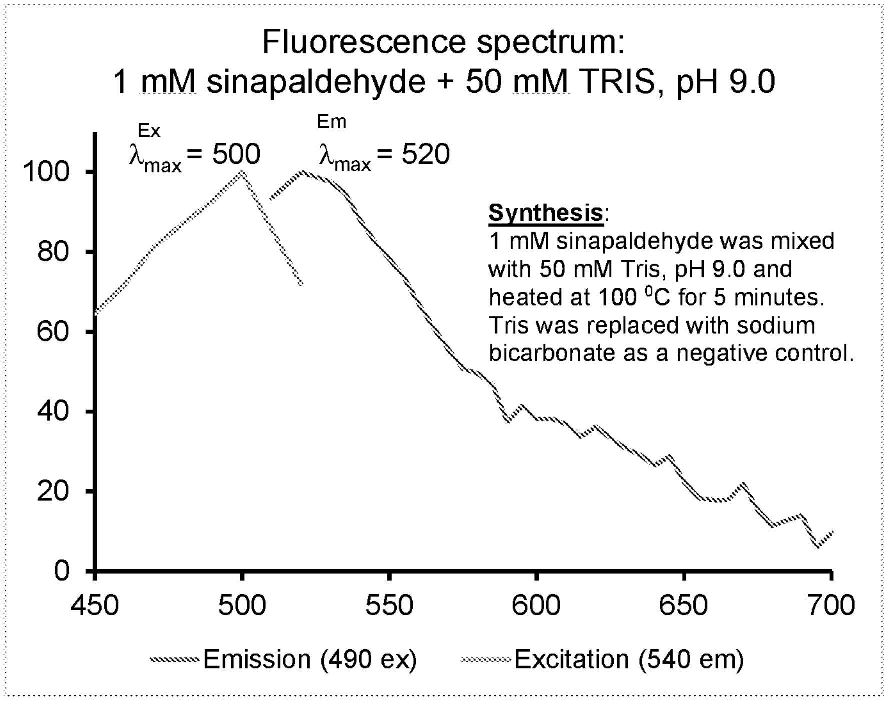
FIG. 10 shows an example of a primary amine, Tris, reacting with sinapaldehyde to form a colored product. (A) Reactions contained 1 mM sinapaldehyde and either 50 mM Tris, pH 9.0 or 50 mM $NaHCO_3$, pH 9.0 and then boiled from 5 minutes prior to taking photographs. (B) Fluorescence excitation and emission spectrum from the products from A after dilution 1:9 in 50 mM $NaHCO_3$, pH 9.0. The emission spectrum was taken from 510-700 nm by using an excitation wavelength of 490 nm. The excitation spectrum was taken from 450-520 nm by recording the emission at 540 nm. (C) Predicted product from condensation between sinapaldehyde and Tris.

1 mM Sinapaldehyde and 50 mM Tris, pH 9.0 were boiled for 5 minutes. Fluorescence excitation and emission spectra after dilution 1:9 in 50 mM $NaHCO_3$, pH 9.0 are shown in FIG. 10. The emission spectrum was taken from 510-700 nm by using an excitation wavelength of 490 nm. The excitation spectrum was taken from 450-520 nm by recording the emission at 540 nm.

Example 17

2 mM Sinapaldehyde was allowed to react with 0.14 mM bovine serum albumin (~8 mM equivalent of free primary amine) in 50 mM Tricine pH 8.5. A red-colored condensation product formed.

Example 18

As shown in FIG. 11A, a FAD-dependent oxidase was identified in the raw nectar of *Nesocodon mauritianus*. The band corresponding to NmNec3 (largest protein) was excised from the gel and subjected to identification via MS-based proteomics methods. The predicted signal peptide that is cleaved from the final protein is underlined in FIG. 11B.

Example 19

Figure 12:
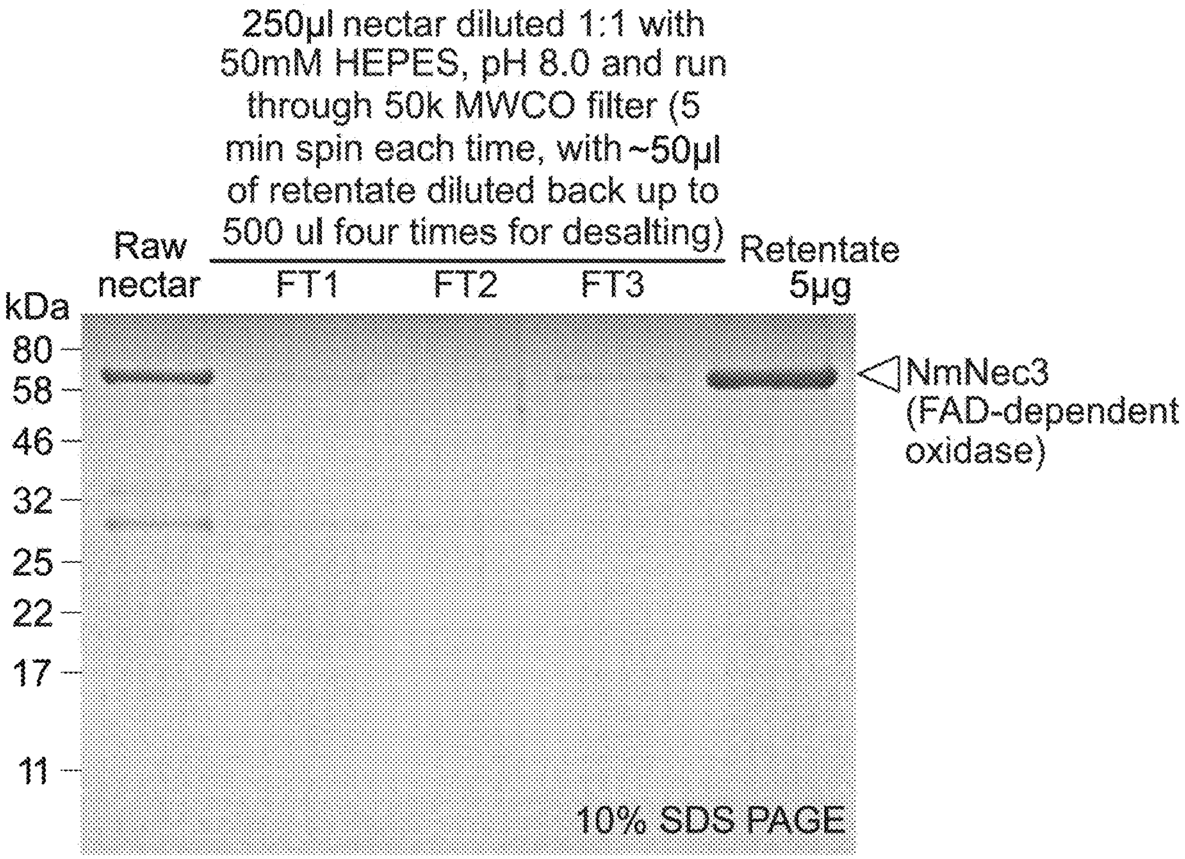
FIG. 12 shows the purification of NmNec3 from the raw nectar of *Nesocodon mauritianus*. Lane 1) Raw nectar (9 mL). Lanes 2-4 (FT1, FT2, FT3): 18 ml of flow through from three successive spins in a 50000 MWCO Amicon® Ultra-0.5 Centrifugal Filter (MilliporeSigma). Lane 5: 5 mg of purified NmNec3.

FIG. 12 shows the purification of NmNec3 from the raw nectar of *Nesocodon mauritianus*. Lane 1) Raw nectar (9 mL). Lanes 2-4 (FT1, FT2, FT3): 18 ml of flow through from three successive spins in a 50000 MWCO Amicon@ Ultra-0.5 Centrifugal Filter (MilliporeSigma). Lane 5: 5 mg of purified NmNec3.

Example 20

Figure 13A:
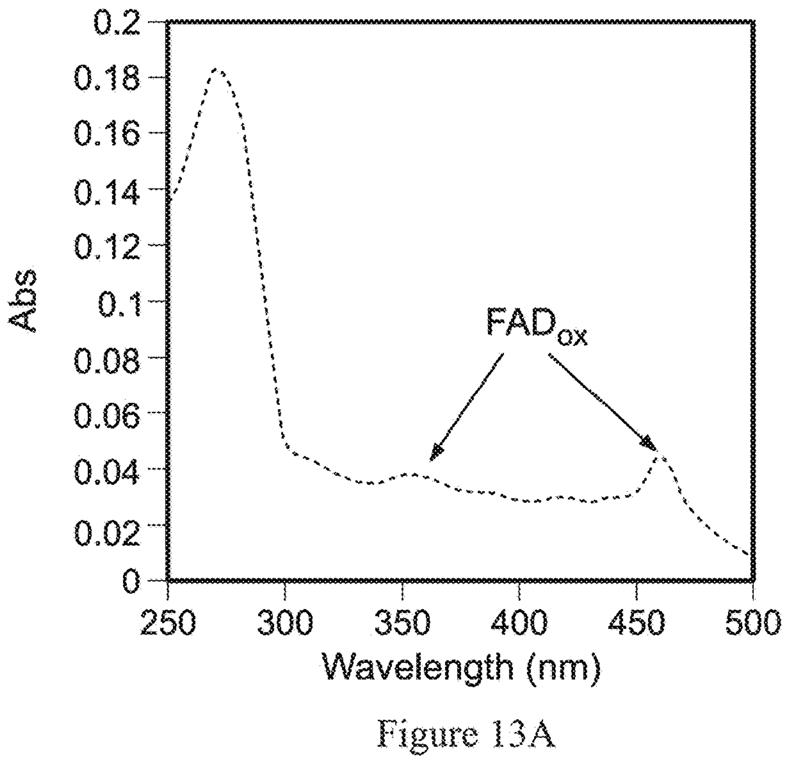
FIG. 13A-13C shows further characterization of NmNec3. (A) Absorbance spectrum of purified NmNec3, with absorbance peaks corresponding to oxidized FAD indicated. (B) In-gel alcohol oxidase activity of NmNec3 with different substrates. (C) Raw red nectar from four different samples (lanes 1-4; 12.5 μL each on 4-20% gel) were subjected to native PAGE (left panel) of followed by activity staining (as in panel B) with 10% ethanol as the substrate. The activity bands from the gel treated with ethanol (left panel, arrowhead) were excised, incubated with 1×SDS PAGE loading buffer and then loaded into lane 2 of the right hand 10% denaturing polyacrylamide gel; M=marker (NEB prestained broad), lane 1 contained 45 μL of raw red nectar. Electrophoresis was performed at 150 V for six hours on a 10% denaturing gel and stained with PAGE BLUE (Thermo). The arrowhead on the right panel indicates the location of protein present in the activity band from the activity gel (right panel), which corresponds to NmNec3.
Figure 13B:
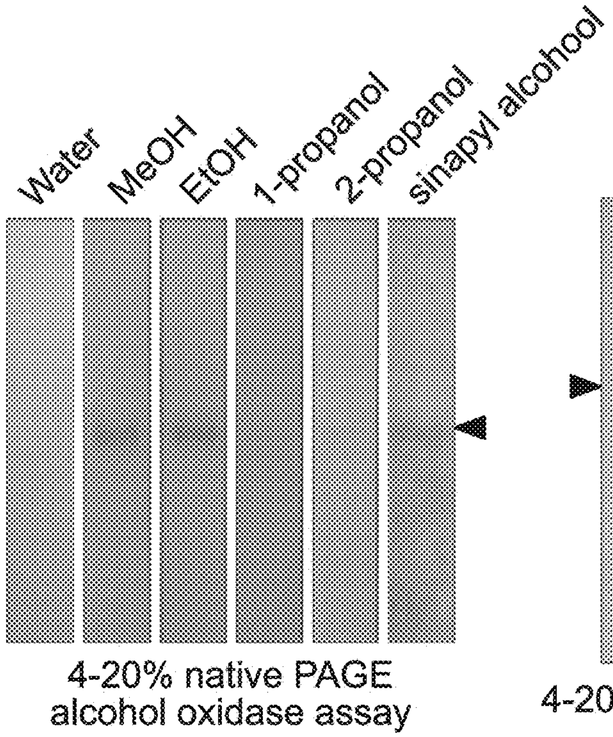
Figure 13C:
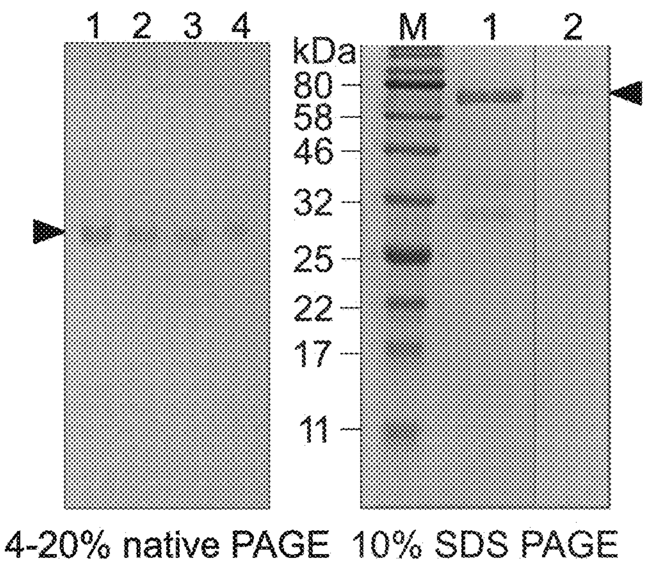

FIG. 13A-13C show further characterization of NmNec3. (A) Absorbance spectrum of purified NmNec3, with absorbance peaks corresponding to oxidized FAD indicated. (B) In-gel alcohol oxidase activity of NmNec3 with different substrates. (C) Raw red nectar from four different samples (lanes 1-4; 12.5 μL each on 4-20% gel) were subjected to native PAGE (left panel) of followed by activity staining (as in panel B) with 10% ethanol as the substrate. The activity bands from the gel treated with ethanol (left panel, arrowhead) were excised, incubated with 1×SDS PAGE loading buffer and then loaded into lane 2 of the right hand 10% denaturing polyacrylamide gel; M=marker (NEB prestained broad), lane 1 contained 45 μL of raw red nectar. Electrophoresis was performed at 150 V for six hours on a 10% denaturing gel and stained with PAGE BLUE (Thermo). The arrowhead on the right panel indicates the location of protein present in the activity band from the activity gel (right panel), which corresponds to NmNec3.

Example 21

Figure 14A:
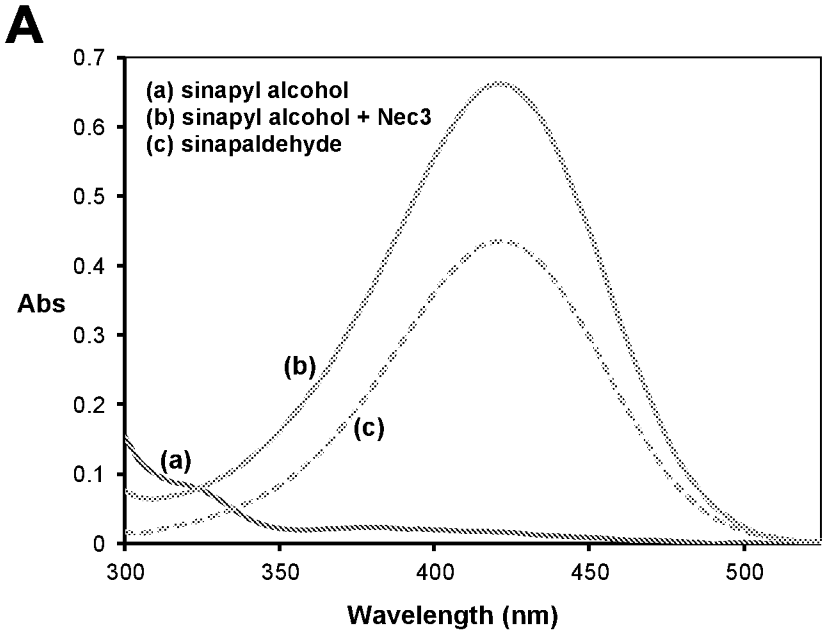
FIG. 14A-14B shows the NmNec3 can oxidize sinapyl alcohol into sinapaldehyde to serve as a precursor to nesocodin. (A) Purified NmNec3 (inset) has sinapyl alcohol oxidase activity and can produce sinapaldehyde. The absorbance spectrum shown by solid yellow line is the result of a reaction mix containing 1 mM sinapyl alcohol and 0.1 μg/mL NmNec3 in 50 mM $Na(H)CO_3$, pH 9.0. Negative controls with sinapyl alcohol but no NmNec3 did not yield any sinapaldehyde (grey line); a 0.5 mM sinapaldehyde standard in 50 mM $Na(H)CO_3$, pH 9.0 was used as a reference. (B) The same reactions as in panel A (with NmNec3), but also containing 10 mM proline, produced a red colored product (solid red line) consistent with both synthetic nesocodin (black dotted line; 1 mM sinapaldehyde plus 10 mM proline) and raw nectar (red dashed line; diluted 1:20).
Figure 14B:
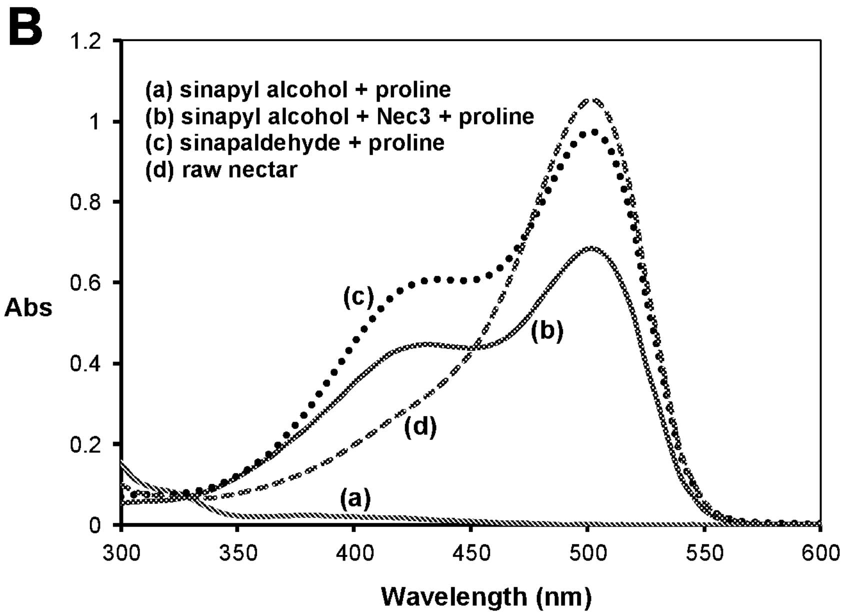

NmNec3 can oxidize sinapyl alcohol into sinapaldehyde to serve as a precursor to nesocodin. 1 mM Sinapyl alcohol was allowed to react with 0.1 μg/mL NmNec3 in 50 mM $Na(H)CO_3$, pH 9.0. The absorbance spectrum of the resulting product showed the formation of sinaptaldehyde (FIG. 14A). A negative control with sinapyl alcohol but no NmNec3 did not yield any sinapaldehyde; a 0.5 mM sinapaldehyde standard in 50 mM $Na(H)CO_3$, pH 9.0 was used as a reference. The same reaction of 1 mM sinapyl alcohol and 0.1 μg/mL NmNec3 in 50 mM $Na(H)CO_3$, pH 9.0, but also containing 10 mM proline, produced a red colored product consistent with synthetic nesocodin (FIG. 14B)

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

(I)

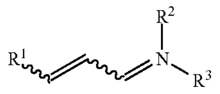

wherein:

$R^1$ is 3,5-dimethoxy-4-hydroxyphenyl;

$R^2$ is selected from the group consisting of, residue of saccharide, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

$R^3$ is absent; or $R^3$ is selected from the group consisting of H, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

or $R^2$ and $R^3$ together with the nitrogen to which they are attached form a 4-10 membered ring heterocycle, wherein heterocycle is optionally substituted with one or more groups independently selected from the group consisting of halo, nitro, carboxy, —OH, cyano, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio, $(C_2\text{-}C_6)$alkanoyloxy, $—NR^aR^b$, $—C({=}O)NH(C_1\text{-}C_6\ alkyl)(S(O)_2R^a)$, $—C({=}O)NH(C_1\text{-}C_6\ alkyl)(C({=}O)\ OR^a)$, $—C({=}O)\ NR^aR^b$, $—OS(O)_3R^a$, $—C({=}O)NH(S(O)_2R^a)$, and $—C({=}O)\ (C_1\text{-}C_6\ alkyl)$, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH, $—NR^aR^b$ and cyano;

provided that when $R^3$ is other than absent, the nitrogen to which $R^3$ is attached is a quaternary nitrogen and is associated with a suitable counter anion $X^-$ to provide a salt;

each $R^a$ and $R^b$ is independently selected from the group consisting of H, $(C_1\text{-}C_6)$alkyl, and $(C_3\text{-}C_6)$cycloalkyl; or $R^a$ and $R^b$ together with the nitrogen to which they are attached form a 4-10 membered ring heterocycle; and X is a suitable counter anion;

provided that the compound is not:

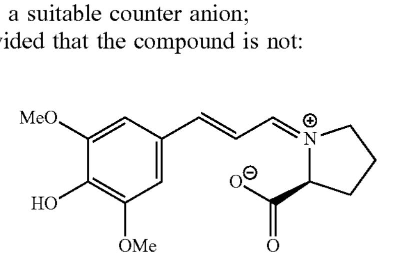

Z-isomer and

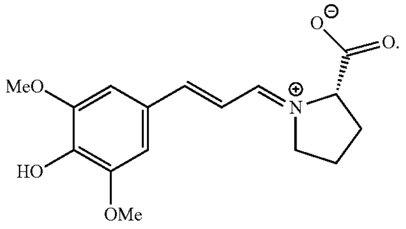

E-isomer

2. A compound of formula (Ia):

(Ia)

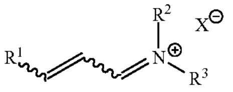

wherein:

$R^1$ is 3,5-dimethoxy-4-hydroxyphenyl;

$R^2$ is selected from the group consisting of H, residue of an amino acid, residue of saccharide, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano;

$R^3$ is selected from the group consisting of H, $(C_1-C_6)$ alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$ alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano;

or $R^2$ and $R^3$ together with the nitrogen to which they are attached form a 4-10 membered ring heterocycle, wherein heterocycle is optionally substituted with one or more groups independently selected from the group consisting of halo, nitro, carboxy, —OH, cyano, $(C_1-C_6)$alkyl, $(C_3-C_6)$cycloalkyl, $(C_1-C_6)$alkoxy, $(C_2-C_6)$ alkenyl, $(C_2-C_6)$alkynyl, $(C_1-C_6)$alkanoyl, $(C_1-C_6)$ alkoxycarbonyl, $(C_1-C_6)$alkylthio, $(C_2-C_6)$ alkanoyloxy, —$NR^aR'$, —C(═O)NH($C_1$-$C_6$ alkyl)(S(O)$_2R^a$), —C(═O)NH($C_1$-$C_6$ alkyl)(C(═O) $OR^a$), —C(═O) $NR^aR^b$, —OS(O)$_3R^a$, —C(═O) NH(S(O)$_2R^a$), and —C(═O) ($C_1$-$C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH, —$NR^aR^b$ and cyano; and each $R^a$ and $R^b$ is independently selected from the group consisting of H, $(C_1-C_6)$alkyl, and $(C_3-C_6)$cycloalkyl; or $R^a$ and $R^b$ together with the nitrogen to which they are attached form a 4-10 membered ring heterocycle; and X is a suitable counter anion.

3. The compound of claim 2 wherein:

$R^2$ is selected from the group consisting of residue of an amino acid, residue of saccharide, $(C_1-C_6)$alkyl, $(C_3-C_6)$cycloalkyl, $(C_1-C_6)$alkoxy, $(C_2-C_6)$alkenyl, $(C_2-C_6)$ alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$ alkoxycarbonyl, $(C_1-C_6)$alkylthio and $(C_2-C_6)$alkanoyloxy is optionally substituted with one or more groups independently selected from the group consisting of halo, carboxy, —OH and cyano.

4. The compound of claim 2 wherein:

$R^2$ is selected from the group consisting of residue of an amino acid, residue of saccharide, $(C_1-C_6)$alkyl, $(C_3-C_6)$cycloalkyl, $(C_1-C_6)$alkoxy, $(C_2-C_6)$alkenyl, $(C_2-C_6)$ alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$ alkoxycarbonyl, $(C_1-C_6)$alkylthio and $(C_2-C_6)$alkanoyloxy is optionally substituted with one or more groups independently selected from the group consisting of halo, carboxy, —OH and cyano; and $R^3$ is selected from the group consisting of $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy, wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano.

5. The compound of claim 2 wherein $R^2$ and $R^3$ together with the nitrogen to which they are attached form a 4-10 membered ring heterocycle, wherein heterocycle is optionally substituted with one or more groups independently selected from the group consisting of halo, nitro, carboxy, —OH, cyano, $(C_1-C_6)$alkyl, $(C_3-C_6)$cycloalkyl, $(C_1-C_6)$ alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —$NR^aR^5$, —C(═O)NH($C_1$-$C_6$ alkyl)(S(O)$_2R^a$), —C(═O)NH($C_1$-$C_6$ alkyl)(C(═O) $OR^a$), —C(═O) $NR^aR^b$, OS(O)$_3R^a$, —C(═O)NH(S(O)$_2R^a$), and —C(═O) ($C_1$-$C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH, —$NR^aR^b$ and cyano.

6. A compound of formula I (I)

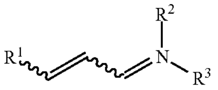

wherein:

$R^1$ is 3,5-dimethoxy-4-hydroxyphenyl;

$R^2$ is $(C_1\text{-}C_6)$alkyl which is optionally substituted with one or more groups independently selected from the group consisting of carboxy and —OH;

$R^3$ is absent; or $R^3$ is selected from the group consisting of H, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

provided that when $R^3$ is other than absent, the nitrogen to which $R^3$ is attached is a quaternary nitrogen and is associated with a suitable counter anion $X^-$ to provide a salt; and X is a suitable counter anion.

7. The compound of claim 6, wherein $R^2$ is s-butyl.

8. A compound of formula I (I)

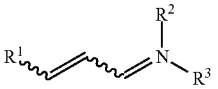

wherein:

$R^1$ is 3,5-dimethoxy-4-hydroxyphenyl;

$R^2$ is carboxymethyl or tris(hydroxymethyl)methyl;

$R^3$ is absent; or $R^3$ is selected from the group consisting of H, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

provided that when $R^3$ is other than absent, the nitrogen to which $R^3$ is attached is a quaternary nitrogen and is associated with a suitable counter anion $X^-$ to provide a salt; and X is a suitable counter anion.

9. A compound of formula I (I)

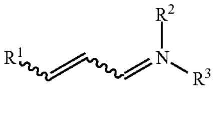

wherein:

$R^1$ is 3,5-dimethoxy-4-hydroxyphenyl;

$R^2$ is selected from the group consisting of H, residue of an amino acid, residue of saccharide, $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_1\text{-}C_6)$alkylthio and $(C_2\text{-}C_6)$alkanoyloxy, wherein any $(C_1\text{-}C_6)$alkyl, $(C_3\text{-}C_6)$cycloalkyl, $(C_1\text{-}C_6)$alkoxy, $(C_2\text{-}C_6)$alkenyl, $(C_2\text{-}C_6)$alkynyl, $(C_1\text{-}C_6)$alkanoyl $(C_1\text{-}C_6)$alkoxycarbonyl, $(C_1\text{-}C_6)$alkylthio and $(C_2\text{-}C_6)$alkanoyloxy is optionally substituted with one or more groups independently selected from the group consisting of halo, carboxy, —OH and cyano;

$R^3$ is $(C_1\text{-}C_6)$alkyl which is optionally substituted with one or more groups independently selected from the group consisting of carboxy and —OH;

provided that the nitrogen to which $R^3$ is attached is a quaternary nitrogen and is associated with a suitable counter anion X to provide a salt; and X is a suitable counter anion.

10. A compound of formula I (I)

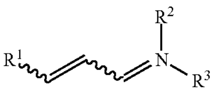

wherein:

$R^1$ is 3,5-dimethoxy-4-hydroxyphenyl;

$R^2$ and $R^3$ together with the nitrogen to which they are attached form a 4-10 membered ring heterocycle, wherein heterocycle is optionally substituted with one or more groups independently selected from the group consisting of carboxy, —OH, $(C_1\text{-}C_6)$alkoxycarbonyl, $(C_2\text{-}C_6)$alkanoyloxy and $—C(=O)(C_1\text{-}C_6\ \text{alkyl})$, wherein any $(C_1\text{-}C_6)$alkoxycarbonyl and $(C_2\text{-}C_6)$alkanoyloxy is optionally substituted with one or more groups independently selected from the group consisting of halo, carboxy, —OH, $—NR^aR^b$ and cyano;

provided that the nitrogen to which $R^3$ is attached is a quaternary nitrogen and is associated with a suitable counter anion X to provide a salt;

each $R^a$ and $R^b$ is independently selected from the group consisting of H, $(C_1\text{-}C_6)$alkyl, and $(C_3\text{-}C_6)$cycloalkyl; or $R^a$ and $R^b$ together with the nitrogen to which they are attached form a 4-10 membered ring heterocycle; and X is a suitable counter anion.

11. A compound or salt selected from:

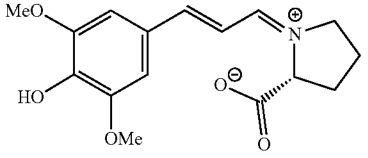

Z-isomer

-continued
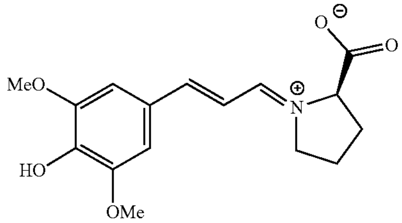
E-isomer
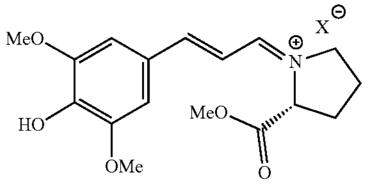
Z-isomer
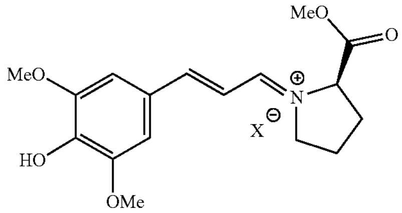
E-isomer
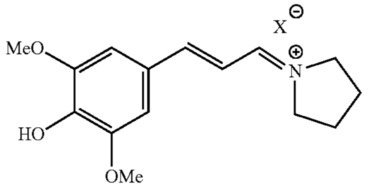
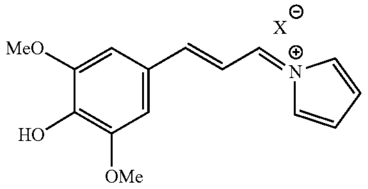
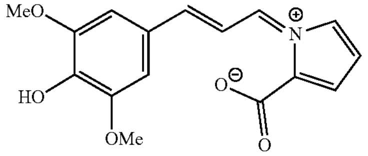
Z-isomer
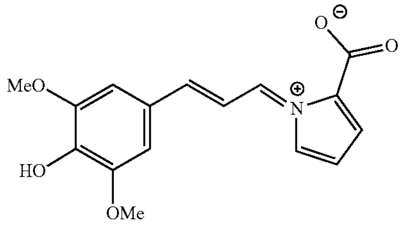
E-isomer
-continued
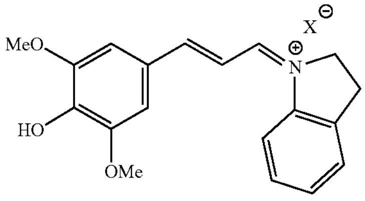
Z-isomer
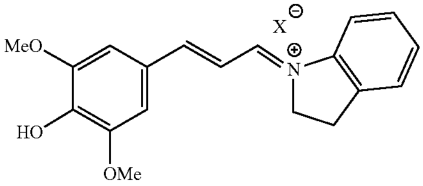
E-isomer
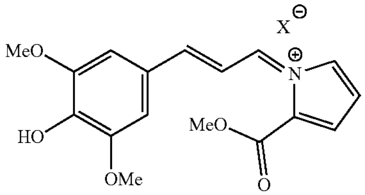
Z-isomer
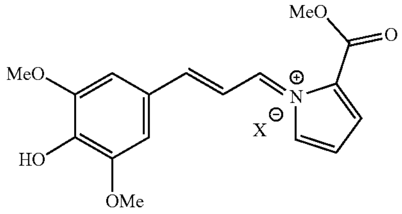
E-isomer
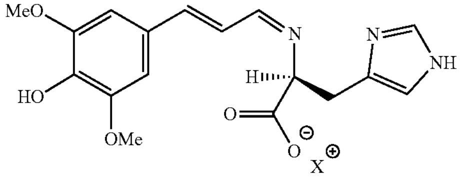
Z-isomer
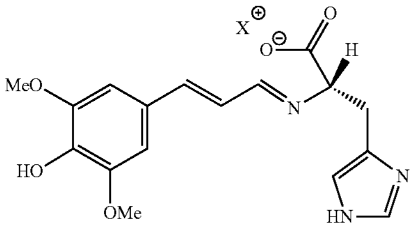
E-isomer
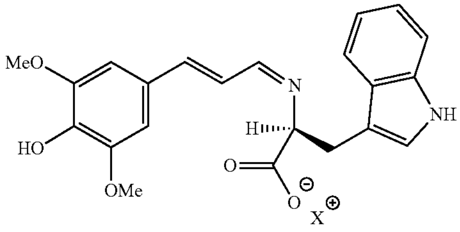
Z-isomer -continued
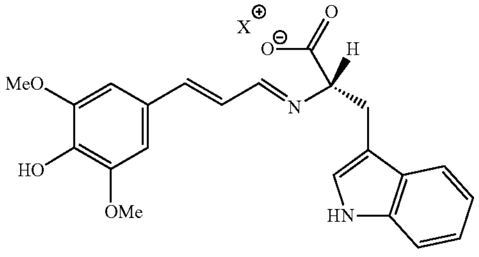
E-isomer
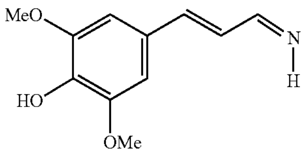
Z-isomer
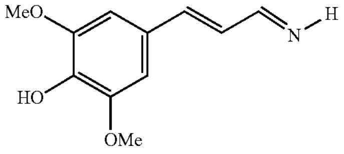
E-isomer
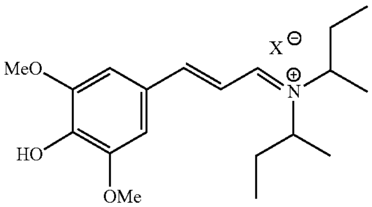
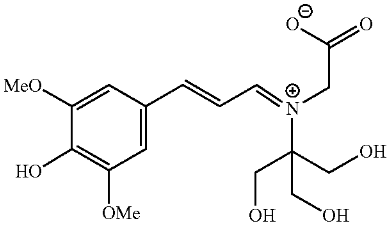
Z-isomer
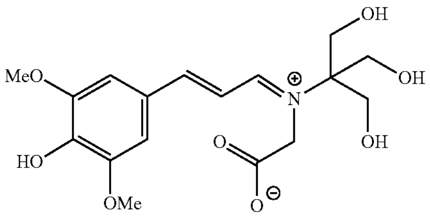
E-isomer
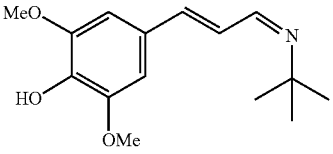
Z-isomer
-continued
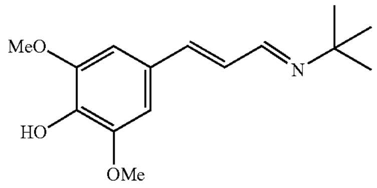
E-isomer
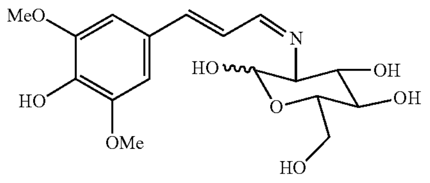
Z-isomer
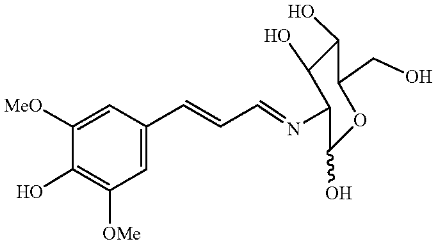
E-isomer
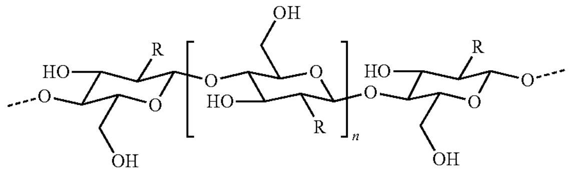
wherein n = 20 to 100
R = $NH_2$ or
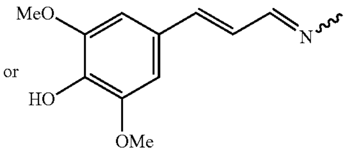
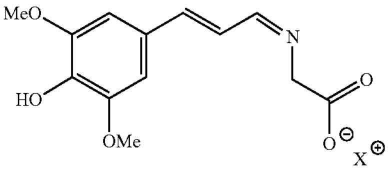
Z-isomer
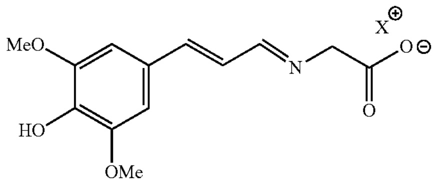
E-isomer
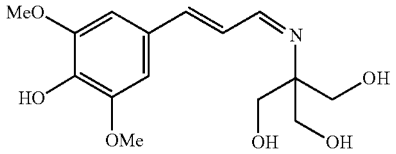
and
Z-isomer -continued

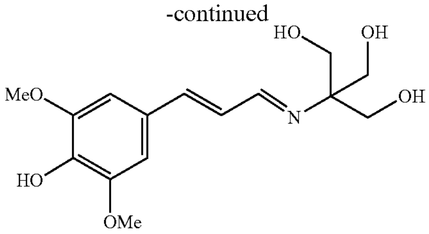

E-isomer wherein at least one R is not $NH_2$ and wherein X is a suitable counter anion.

12. A food dye comprising a compound of formula (I), as described in claim 1.

13. The compound of claim 1, wherein $R^3$ is absent.

14. A food dye comprising a compound of formula (Ia), as described in claim 2.

15. A food dye comprising a compound of formula (I), as described in claim 6.

16. A food dye comprising a compound of formula (I), as described in claim 8.

17. A food dye comprising a compound of formula (I), as described in claim 9.

18. A food dye comprising a compound of formula (I), as described in claim 10.

* * * * *

SEQUENCE LISTING

<160> NUMBER OF SEQ ID NOS: 1

<210> SEQ ID NO 1
<211> LENGTH: 558
<212> TYPE: PRT
<213> ORGANISM: Nesocodon mauritianus

<400> SEQUENCE: 1

Met Ala Thr Met Ala Ile Leu Gln Arg Thr Phe Ser Phe Ile Leu Ile
1 5 10 15

Phe Ser Ile Ala Leu His Leu Lys Ser Leu Phe Ala Met Glu Thr Asp
20 25 30

Ser Gly Ala Glu Leu Lys Tyr Leu Glu Leu Ile His Glu Ala Asn Glu
35 40 45

Phe Thr Pro Asp Glu Glu Tyr Asp Tyr Ile Val Val Gly Gly Gly Thr
50 55 60

Ala Gly Cys Pro Leu Ala Ala Thr Leu Ser Glu Asn Tyr Ser Val Leu
65 70 75 80

Val Leu Glu Arg Gly Gly Asp Gln His Ser His Pro Asn Ile Ile Arg
85 90 95

Gln Glu Asn Val Ala Asn Asn Ala Leu Pro Ala Asp Asp Glu Asn Ser
100 105 110

Pro Ser Gln Ala Phe Thr Ser Glu Asp Gly Val Pro Gly Leu Val Arg
115 120 125

Gly Arg Val Leu Gly Gly Ser Ser Met Ile Asn Phe Gly Phe Tyr Ser
130 135 140

Arg Gly Asp Asp Tyr Phe Phe Lys Asn Thr Gly Ile Glu Trp Asp Met
145 150 155 160

Asp Ser Val Lys Thr Ala Tyr Glu Trp Val Glu Glu Thr Leu Val His
165 170 175

Arg Pro Asp Asn Val Ser Thr Trp Glu Ser Ser Val Arg Asp Ala Leu
180 185 190

Leu Glu Val Gly Val Leu Pro Asp Asn Gly Asn Thr Leu Asp His Leu
195 200 205

Val Gly Thr Lys Val Ser Gly Ser Thr Phe Asp Ser Thr Gly Asn Arg
210 215 220

His Gly Ala Val Glu Leu Leu Asn Lys Ala Asn Pro Asn Asn Leu Arg
225 230 235 240

Val Ile Val His Ala Thr Val Asp Arg Ile Ile Phe Ser Ser Ser Glu
245 250 255

Ser Ser Gly Pro Ser Val Val Arg Val Val Tyr His Asp Ser His Gly
260 265 270

Lys Ser Tyr Gln Val Gly Ile Arg Glu Asn Gly Glu Val Ile Leu Ser
275 280 285

Ala Gly Ala Phe Gly Ser Pro Gln Leu Leu Leu Val Ser Gly Val Gly
290 295 300

Pro Ser Gln Asn Leu Thr Ser Leu Glu Ile Pro Val Val His Asp Gln
305 310 315 320

Pro Phe Val Gly Gln Tyr Met Ile Asp Asn Pro Arg Ile Asn Leu Ala
325 330 335

Leu Met Leu Pro Phe Ser Val Val Asp Ser Gly Thr Pro Val Val Gly
340 345 350

Ile Thr Gly Lys Gly Ser Tyr Ile Glu Thr Thr Ser Ser Ser Thr Pro
355 360 365

-continued

```
Phe Thr Ser Pro Val Ser Pro Leu Tyr Phe Pro Tyr Pro Tyr Pro Pro
    370                 375                 380

Val Asn Ile Ser Met Gly Tyr Phe Phe Gly Lys Val Ser Asn Pro Thr
385                 390                 395                 400

Ser Ala Gly Ser Leu Trp Leu Lys Ser Pro Ser Asp Val Ala Ile Thr
                405                 410                 415

Pro Ser Val Arg Phe Asn Tyr Phe Ser Lys Pro Glu Asp Val His Gln
            420                 425                 430

Cys Ala Asp Ala Val Ala Thr Tyr Glu Lys Ile Leu Lys Thr Lys Ala
        435                 440                 445

Met Glu Met Tyr Lys Phe Lys Asp His Gly Gly Glu Lys Tyr Phe Gln
    450                 455                 460

Ile Val Gly Arg Gln Ile Pro Glu Asn Thr Ser Asp Phe Glu Ser Met
465                 470                 475                 480

Ala Thr Tyr Cys Arg Lys Thr Val Thr Thr Phe Tyr His Tyr Cys Gly
                485                 490                 495

Gly Cys Thr Val Asn Lys Val Val Asp Ser Asn Leu Lys Val Val Gly
            500                 505                 510

Ile Gly Gly Leu Arg Val Val Asp Asn Ser Val Phe Thr Ser Ser Pro
        515                 520                 525

Gly Thr Asn Pro Gln Ala Thr Thr Met Met Leu Gly Arg Tyr Met Gly
    530                 535                 540

Val Lys Ile Gln Gln Glu Arg Ala Gly Ser Asp Gly Asp Asn
545                 550                 555
```